(12) United States Patent
McNamara et al.

(10) Patent No.: US 9,358,371 B2
(45) Date of Patent: *Jun. 7, 2016

(54) INTRA-ATRIAL IMPLANTS MADE OF NON-BRAIDED MATERIAL

(71) Applicant: Corvia Medical, Inc., Tewksbury, MA (US)

(72) Inventors: Edward McNamara, Chelmsford, MA (US); David Celermajer, Vaucluse (AU); Stephen J. Forcucci, Winchester, MA (US); Hiroatsu Sugimoto, Cambridge, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 506 days.

This patent is subject to a terminal disclaimer.

(21) Appl. No.: 13/744,791

(22) Filed: Jan. 18, 2013

(65) Prior Publication Data

US 2013/0231737 A1     Sep. 5, 2013

Related U.S. Application Data

(63) Continuation of application No. 12/848,084, filed on Jul. 30, 2010, which is a continuation of application No. 12/719,843, filed on Mar. 8, 2010, now Pat. No. 8,157,860.

(60) Provisional application No. 61/240,085, filed on Sep. 4, 2009.

(51) Int. Cl.
*A61F 2/24*     (2006.01)
*A61M 27/00*     (2006.01)

(Continued)

(52) U.S. Cl.
CPC .......... *A61M 27/002* (2013.01); *A61B 17/0057* (2013.01); *A61F 2/06* (2013.01);
(Continued)

(58) Field of Classification Search
CPC ....................................................... A61F 2/24
USPC ....................................................... 623/1.26
See application file for complete search history.

(56) References Cited

U.S. PATENT DOCUMENTS

| 3,874,388 A | 4/1975 | King et al. |
| 4,018,228 A | 4/1977 | Goosen |

(Continued)

FOREIGN PATENT DOCUMENTS

| AU | 2007317191 A1 | 5/2008 |
| CN | 1218379 A | 6/1999 |

(Continued)

OTHER PUBLICATIONS

European Application Serial No. 10772411.4, European Search Opinion and Supplementary European Search Report mailed Mar. 16, 2012, 5 pages.

(Continued)

*Primary Examiner* — Matthew Schall
(74) *Attorney, Agent, or Firm* — Shay Glenn LLP

(57) ABSTRACT

Several unique intra-cardiac pressure devices, placement catheters, methods of placement and methods of treating heart failure are presented. The intra-cardiac pressure devices presented allow sufficient flow from the left atrium to the right atrium to enable the relief of elevated left atrial pressure and resulting patient symptoms. The intra-cardiac pressure devices are made of a non-braided material.

12 Claims, 30 Drawing Sheets

(51) Int. Cl.
*A61B 17/00* (2006.01)
*A61F 2/06* (2013.01)

(52) U.S. Cl.
CPC .............. *A61F 2/24* (2013.01); *A61F 2/2412* (2013.01); *A61F 2/2442* (2013.01); *A61F 2/2475* (2013.01); *A61B 2017/00252* (2013.01); *A61B 2017/00575* (2013.01); *A61B 2017/00592* (2013.01); *A61B 2017/00606* (2013.01); *A61B 2017/00867* (2013.01)

(56) References Cited

U.S. PATENT DOCUMENTS

| | | | |
|---|---|---|---|
| 4,373,216 A | 2/1983 | Klawitter |
| 4,491,986 A | 1/1985 | Gabbay |
| 4,705,507 A | 11/1987 | Boyles |
| 5,100,423 A | 3/1992 | Fearnot |
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,556,386 A | 9/1996 | Todd |
| 5,556,408 A | 9/1996 | Farhat |
| 5,578,045 A | 11/1996 | Das |
| 5,693,090 A | 12/1997 | Unsworth et al. |
| 5,702,412 A | 12/1997 | Popov et al. |
| 5,725,552 A | 3/1998 | Kotula et al. |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich, Jr. et al. |
| 6,059,827 A | 5/2000 | Fenton |
| 6,068,635 A | 5/2000 | Gianotti |
| 6,077,281 A | 6/2000 | Das |
| 6,120,534 A | 9/2000 | Ruiz |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,241,678 B1 | 6/2001 | Afremov et al. |
| 6,258,119 B1 | 7/2001 | Hussein et al. |
| 6,286,512 B1 | 9/2001 | Loeb et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,301 B1 | 10/2002 | Amplatz et al. |
| 6,468,303 B1 | 10/2002 | Amplatz et al. |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,641,610 B2 | 11/2003 | Wolf et al. |
| 6,645,143 B2 | 11/2003 | VanTassel et al. |
| 6,666,885 B2 | 12/2003 | Moe |
| 6,712,836 B1 | 3/2004 | Berg et al. |
| 6,719,768 B1 | 4/2004 | Cole et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,001,409 B2 | 2/2006 | Amplatz |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,159,593 B2 | 1/2007 | McCarthy et al. |
| 7,226,466 B2 | 6/2007 | Opolski |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,524,330 B2 | 4/2009 | Berreklouw |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |
| 7,766,966 B2 | 8/2010 | Richelsoph |
| 7,819,890 B2 | 10/2010 | Russo et al. |
| 7,842,026 B2 | 11/2010 | Cahill et al. |
| 7,871,419 B2 | 1/2011 | Devellian et al. |
| 7,905,901 B2 | 3/2011 | Corcoran et al. |
| 7,927,370 B2 | 4/2011 | Webler et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,052,750 B2 | 11/2011 | Tuval et al. |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,252,042 B2 | 8/2012 | McNamara et al. |
| 8,303,623 B2 | 11/2012 | Melzer et al. |
| 8,313,505 B2 | 11/2012 | Amplatz et al. |
| 8,366,088 B2 | 2/2013 | Allen et al. |
| 8,398,670 B2 | 3/2013 | Amplatz et al. |
| 8,460,372 B2 | 6/2013 | McNamara et al. |
| 8,777,974 B2 | 7/2014 | Amplatz et al. |
| 2001/0029368 A1 | 10/2001 | Berube |
| 2002/0029061 A1 | 3/2002 | Amplatz et al. |
| 2002/0062135 A1 | 5/2002 | Mazzocchi et al. |
| 2002/0072765 A1 | 6/2002 | Mazzocchi et al. |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0095173 A1 | 7/2002 | Mazzocchi et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2002/0198563 A1 | 12/2002 | Gainor et al. |

(56) References Cited

U.S. PATENT DOCUMENTS

| | | |
|---|---|---|
| 2003/0093072 A1 | 5/2003 | Friedman |
| 2003/0125798 A1 | 7/2003 | Martin |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | Mccarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamolo et al. |
| 2005/0049697 A1 | 3/2005 | Sievers |
| 2005/0065507 A1 | 3/2005 | Hartley et al. |
| 2005/0065548 A1 | 3/2005 | Marino et al. |
| 2005/0065589 A1 | 3/2005 | Schneider et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0096735 A1 | 5/2005 | Hojeibane et al. |
| 2005/0113868 A1 | 5/2005 | Devellian et al. |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0165344 A1 | 7/2005 | Dobak, III |
| 2005/0187616 A1 | 8/2005 | Realyvasquez |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267523 A1 | 12/2005 | Devellian et al. |
| 2005/0267524 A1 | 12/2005 | Chanduszko |
| 2005/0273075 A1 | 12/2005 | Krulevitch et al. |
| 2005/0288722 A1 | 12/2005 | Eigler et al. |
| 2006/0004323 A1 | 1/2006 | Chang et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0085060 A1 | 4/2006 | Campbell |
| 2006/0095066 A1 | 5/2006 | Chang et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0016250 A1 | 1/2007 | Blaeser et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0168019 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249397 A1 | 10/2008 | Kapadia |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018562 A1 | 1/2009 | Amplatz et al. |
| 2009/0018570 A1 | 1/2009 | Righini et al. |
| 2009/0025820 A1 | 1/2009 | Adams |
| 2009/0030495 A1 | 1/2009 | Koch |
| 2009/0054984 A1 | 2/2009 | Shortkroff et al. |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0131978 A1 | 5/2009 | Gainor et al. |
| 2009/0171386 A1 | 7/2009 | Amplatz et al. |
| 2009/0177269 A1 | 7/2009 | Kalmann et al. |
| 2009/0187214 A1 | 7/2009 | Amplatz et al. |
| 2009/0209855 A1 | 8/2009 | Drilling et al. |
| 2009/0209999 A1 | 8/2009 | Afremov |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul, Jr. et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030259 A1 | 2/2010 | Pavcnik et al. |
| 2010/0030321 A1 | 2/2010 | Mach |
| 2010/0049307 A1 | 2/2010 | Ren |
| 2010/0051886 A1 | 3/2010 | Cooke et al. |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249490 A1 | 9/2010 | Farnan |
| 2010/0249491 A1 | 9/2010 | Farnan et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0268316 A1 | 10/2010 | Brenneman et al. |
| 2010/0274351 A1 | 10/2010 | Rolando et al. |

(56) References Cited

U.S. PATENT DOCUMENTS

| | | |
|---|---|---|
| 2010/0298755 A1 | 11/2010 | McNamara et al. |
| 2010/0305685 A1 | 12/2010 | Millwee et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0087261 A1 | 4/2011 | Wittkampf et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0184439 A1 | 7/2011 | Anderson et al. |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | Mcnamara |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | Mcnamara et al. |
| 2012/0130301 A1 | 5/2012 | Mcnamara et al. |
| 2012/0165928 A1 | 6/2012 | Nitzan et al. |
| 2012/0259263 A1 | 10/2012 | Celermajer et al. |
| 2012/0265296 A1 | 10/2012 | Mcnamara et al. |
| 2012/0289882 A1 | 11/2012 | Mcnamara et al. |
| 2012/0290062 A1 | 11/2012 | Mcnamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0267885 A1 | 10/2013 | Celermajer et al. |
| 2014/0012368 A1 | 1/2014 | Sugimoto et al. |
| 2014/0194971 A1 | 7/2014 | McNamara |
| 2014/0257167 A1 | 9/2014 | Celermajer et al. |
| 2014/0277054 A1 | 9/2014 | McNamara et al. |
| 2015/0039084 A1 | 2/2015 | Levi et al. |
| 2015/0119796 A1 | 4/2015 | Finch |

FOREIGN PATENT DOCUMENTS

| | | |
|---|---|---|
| CN | 1556719 A | 12/2004 |
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| CN | 102905626 A | 1/2013 |
| CN | 102908213 A | 2/2013 |
| EP | 1264582 A2 | 2/2002 |
| EP | 1470785 A1 | 10/2004 |
| EP | 1849440 A1 | 10/2007 |
| EP | 2528646 A2 | 12/2012 |
| EP | 2537490 A1 | 12/2012 |
| JP | 58-27935 U | 6/1983 |
| JP | 2003530143 | 10/2003 |
| WO | 9527448 A1 | 10/1995 |
| WO | WO98/08456 A1 | 3/1998 |
| WO | WO98/42403 A1 | 10/1998 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | 2008055301 A1 | 5/2008 |
| WO | 2008058940 A1 | 5/2008 |
| WO | 2010111666 A1 | 9/2010 |
| WO | 2010128501 A1 | 11/2010 |
| WO | 2010129089 A2 | 11/2010 |
| WO | WO2010/129511 A2 | 11/2010 |
| WO | 2011093941 A2 | 8/2011 |
| WO | 2011094521 A2 | 8/2011 |
| WO | 2011093941 A3 | 10/2011 |
| WO | 2011093941 A4 | 12/2011 |
| WO | 2011094521 A3 | 12/2011 |
| WO | 2012071075 A1 | 5/2012 |
| WO | 2012109557 A2 | 8/2012 |
| WO | 2012109557 A3 | 1/2013 |
| WO | 2013096965 A1 | 6/2013 |

OTHER PUBLICATIONS

Ad et al., "A one way valved atrial septal patch: A new surgical technique and its clinical application", The Journal of Thoracic and Cardiovascular Surgery, vol. 111, Apr. 1996, pp. 841-848.

Althoff et al., "Long-Term follow up of a fenestrated amplatzer atrial septal occluder in pulmonary arterial hypertension", American College of Chest Physicians 2008, Chest, vol. 133, No. 1, Jan. 2008, 5 pages.

Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.

Bailey, Steven R., "Nanotechnology in prosthetic heart valves", EuroPCR 2005, May 24-27, 2005, 31 pages.

Bolling, Steven F., "Direct Flow medical—my valve is better", Direct Flow medical Inc., Apr. 23, 2009, 21 pages.

Caselli, Joseph S., "No! valve replacement: patient prosthetic mismatch rarely occurs", Texas Heart Institute, Apr. 25, 2009, 75 pages.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Design News, "Low Power Piezo Motion", http://www.designnews.com/document.asp?doc_id=229053&dfpPParams&dfpPParams=ht_13,aid_229053&dfpLayout=article, May 14, 2010, 3 pages.

European Application Serial No. EP12180631.9, European Search Report mailed Nov. 19, 2012, 5 pages.

Gaudiani et al., "A philosophical approach to mitral valve repair", Dallas-Leipzig International Valve Congress, Apr. 24, 2009, 28 pages.

Hijazi, Ziyad M., "Valve Implantation", Pediatric & Adult Interventional Therapies for Congenital and Valvular Heart. Disease, Jul. 22-25, 2007, 36 pages.

Larios et al., "The Use of an Artificial Foraminal Valve Prosthesis in the Closure of Interatrial and Interventricular Septal Defects", American College of Chest Physicians, Dis. Chest. 1959, vol. 36, Dec. 1959, 12 pages.

Leon, Martin B., "Transcatheter Aortic Valve Therapy: Summary Thoughts", Transcatheter Valve Therapies, Jun. 24-26, 2009, 19 pages.

Merchant et al., "Advances in Arrhythmia and Electrophysiology; Implantable Sensors for Heart Failure", Circ. Arrhythm. Electrophysiol., vol. 3, Dec. 2010, pp. 657-667.

Moses, Jeffrey W., "The Good, the Bad and the ugly of transcatheter AVR", Jul. 10, 2009, 28 pages.

O'Loughlin et al., "Insertion of a Fenestrated Amplatzer Atrial Sestosotomy Device for Severe Pulmonary Hypertension", Heart ,Lung and Circulation, vol. 15, 2006, pp. 275-277.

Park et al., "Blade atrial septostomy: collaborative study", Circulation, Journal of the American Heart Association, vol. 66, No. 2, Aug. 1982, pp. 258-266.

International Application Serial No. PCT/AU2007/001704, International Search Report mailed Jan. 16, 2008, 4 pages.

(56) References Cited

OTHER PUBLICATIONS

International Application Serial No. PCT/AU2007/01704, International Preliminary Report on Patentability mailed Aug. 22, 2008, 5 pages.
International Application Serial No. PCT/AU2007/01704, Written Opinion mailed Jan. 16, 2008, 5 pages.
International Application Serial No. PCT/US10/58110, International Preliminary Report on Patentability mailed Nov. 27, 2012, 11 pages.
International Application Serial No. PCT/US2010/026574, International Preliminary Report on Patentability mailed Nov. 10, 2011, 7 pages.
International Application Serial No. PCT/US2010/026574, International Search Report and Written Opinion mailed Nov. 19, 2010, 9 pages.
International Application Serial No. PCT/US2010/58110, International Search Report and Written Opinion mailed Aug. 26, 2011, 14 pages.
International Application Serial No. PCT/US2011/041841, International Search Report and Written Opinion mailed Feb. 9, 2012, 12 pages.
International Application Serial No. PCT/US2011/22895, International Search Report and Written Opinion mailed Oct. 24, 2011, 11 pages.
International Application Serial No. PCT/US2012/024680, International Search Report and Written Opinion mailed Oct. 23, 2012, 11 pages.
Pedra et al., "Stent Implantation to Create Interatrial Communications in Patients With Complex Congenital Heart Disease", Catheterization and Cardiovascular Interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1066.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Stone, Gregg W., "Transcatheter devices for mitral valve repair surveying the landscape", Columbia University Medical Center, Jul. 10, 2009, 48 pages.
Stormer et al., "Comparative Study of in vitro Flow Characteristics between a Human Aortic Valve and a Designed Aortic Valve and Six Corresponding Types of Prosthetic Heart Valves", Eur. Surg. Res., vol. 8, No. 2, 1976, 117-131.
Watterson et al., "Very Small Pulmonary Arteries: Central End-to-Side Shunt", Ann. Thorac. Surg., vol. 52, No. 5, Nov. 1991, pp. 1132-1137.
McNamara et al.; U.S. Appl. No. 14/612,022 entitled "Methods and devices for intra-atrial shunts having adjustable sizes," filed Feb. 2, 2015.
PCT/US2011/041841, International Application Serial No. PCT /US2011/041841, International Preliminary Report on Patentability and Written Opinion mailed Jun. 6, 2013, DC Devices, Inc. et al, 8 pages.
PCT/US2012/071588, International Application Serial No. PCT/US2012/071588, International Search Report and Written Opinion mailed Apr. 19, 2013, DC Devices, Inc., 19 pages.
Ad et al.; A one way valved atrial septal patch: A new surgical technique and its clinical application; The Journal of Thoracic and Cardiovascular Surgery; 111; pp. 841-848; Apr. 1996.
Althoff et al.; Long-term follow up of a fenestrated amplatzer atrial septal occluder in pulmonary arterial hypertension; Chest; 133(1); pp. 183-185; Jan. 2008.
Atz et al.; Preoperative management of pulmonary venous hypertension in hypoplastic left heart syndrome with restrictive atrial septal defect; the American Journal of Cardiology; 83; pp. 1224-1228; Apr. 15, 1999.
Physik Instrumente; Piezo for Motion Control in Medical Design and Drug Research (product information); Physik Instrumente (PI) GmbH & Co. KG; 22 pgs.; © Nov. 21, 2010.
Roven et al.; Effect of compromising right ventricular function in left ventricular failure by means of interatrial and other shunts; Am J Cardiol.; 24(2); pp. 209-219; Aug. 1969.
Sambhi et al.; Pathologic Physiology of Lutembacher Syndrome; Am J Cardiol.; 2(6); pp. 681-686; Dec. 1958.
Webber, Ralph; Piezo Motor Based Medical Devices; Medical Design Technology; 5 pgs.; Apr. 2, 2009; retrieved from the internet on Jul. 19, 2012 (http://mdtmag.com/articles/2009/04/piezo-motor-based-medical-devices).
Celermajer et al.; U.S. Appl. No. 14/498,903 entitled "Apparatus and methods to create and maintain an intra-atrial pressure relief opening," filed Sep. 26, 2014.
PCT/US12/024680, International Application Serial No. PCT/US12/024680, International Preliminary Report on Patentability and Written Opinion mailed Aug. 22, 2013, DC Devices, Inc, 7 pages.
Forcucci et al.; U.S. Appl. No. 14/807,544 entitled "Devices and methods for treating heart failure," filed Jul. 23, 2015.
Finch; U.S. Appl. No. 14/645,416 entitled "Devices and methods for treating heart failure," filed Mar. 11, 2015.

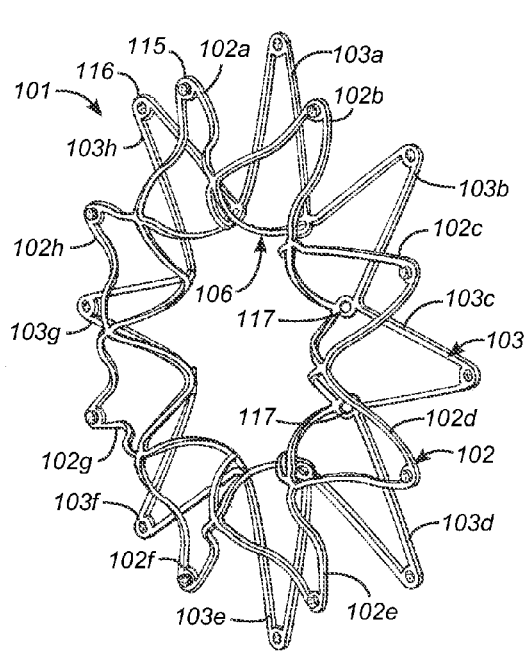
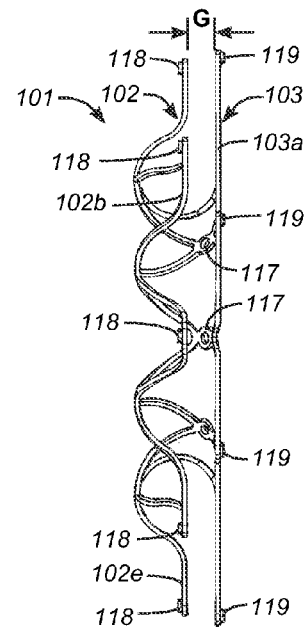
FIG. 4   FIG. 5
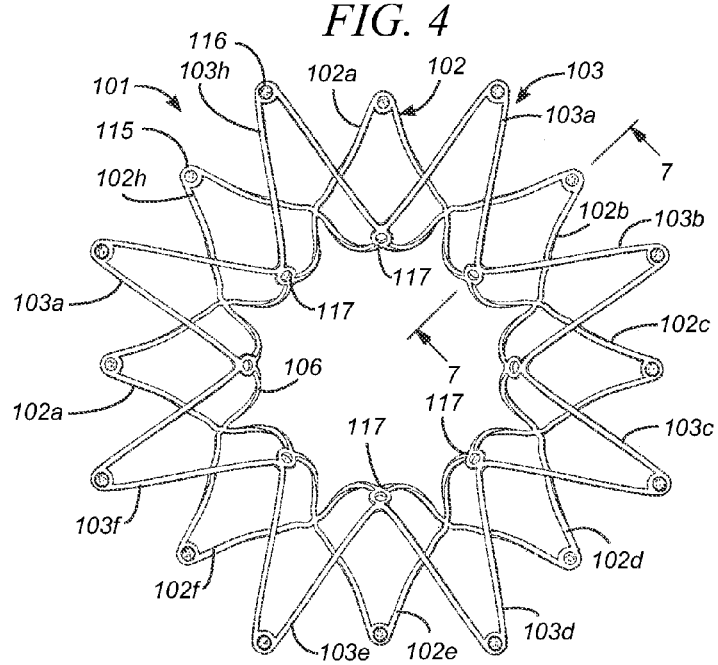
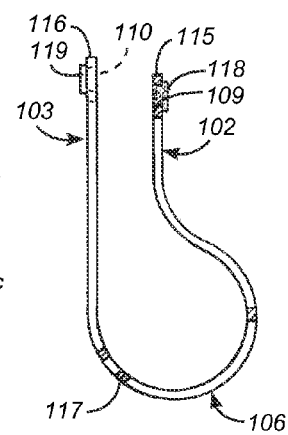
FIG. 6   FIG. 7

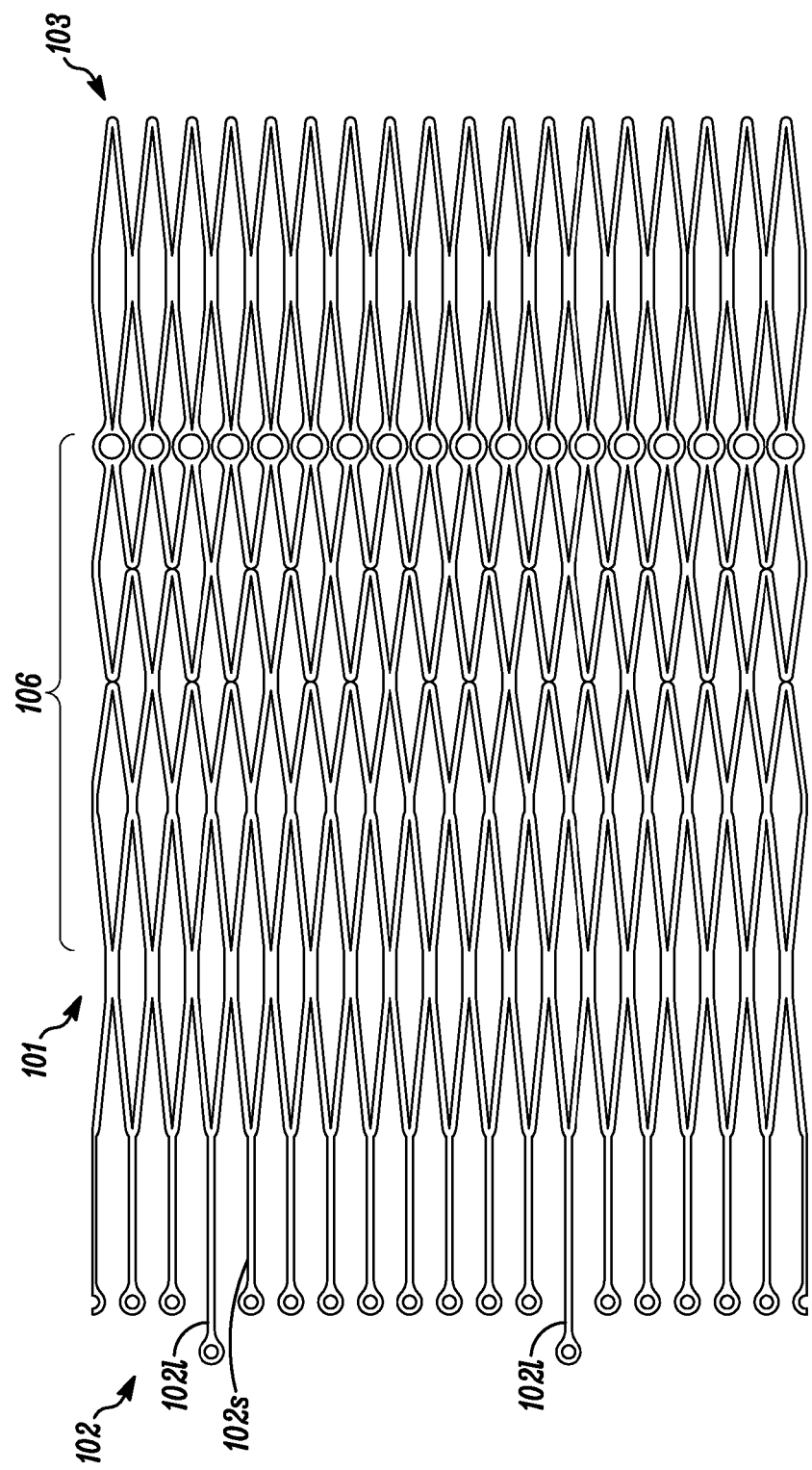

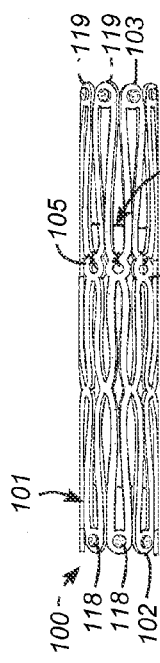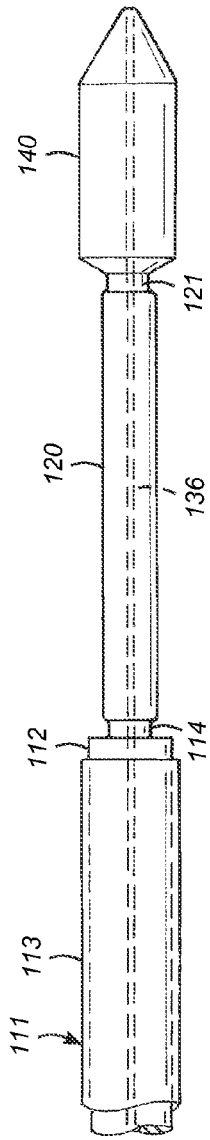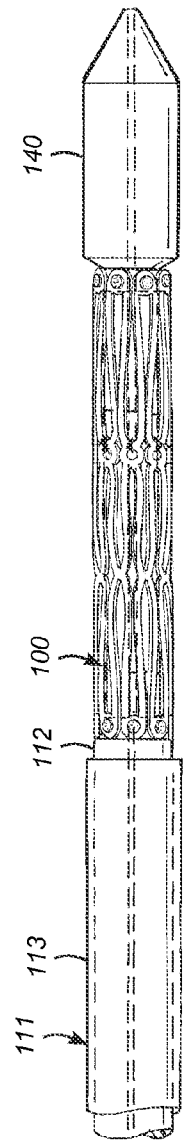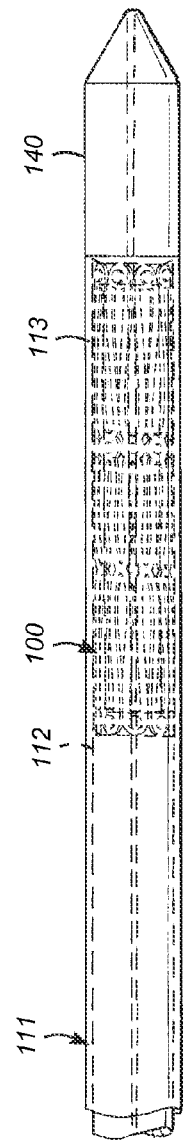

INTRA-ATRIAL IMPLANTS MADE OF NON-BRAIDED MATERIAL

CROSS REFERENCE TO RELATED APPLICATIONS

This application is a continuation of U.S. patent application Ser. No. 12/848,084, filed Jul. 30, 2010, which is a continuation of U.S. patent application Ser. No. 12/719,843, filed Mar. 8, 2010, which claims the benefit of U.S. Provisional Patent Application No. 61/240,085, filed Sep. 4, 2009, each of which is hereby incorporated herein by reference in its entirety.

The present application incorporates by reference the following applications: U.S. application Ser. No. 12/447,617 filed Apr. 28, 2009, International Application No. PCT/AU2007/001704 filed Nov. 7, 2007 and Australian Patent Application No. AU 2006906202 filed Nov. 7, 2006.

FIELD OF THE INVENTION

The present invention relates generally to devices and methods for treating heart failure. In particular, the invention relates to interatrial pressure vents, shunts and the like, which reduce elevated pressure on one side of the heart thus mitigating the symptoms that result, as well as placement devices, systems, and methods therefore.

BACKGROUND OF THE INVENTION

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. In addition to diastolic heart failure, a number of other medical conditions, including systolic dysfunction of the left ventricle and valve disease, can lead to elevated pressures in the left atrium. Increased left atrial pressure often causes acute or chronic breathlessness amongst other problems. In addition, a variety of heart conditions can lead to "right heart failure", which can result in enlargement of the liver (hepatomegaly), fluid accumulation in the abdomen (ascites) and/or swelling of the lower limbs.

Frequently, patients with diastolic heart failure experience breathlessness due, in part, to elevated pulmonary venous pressure. These patients often feel worse when supine than when sitting or standing, implying that small changes in pulmonary venous pressure have a pronounced effect on symptoms.

In the past, strategies have been described for the relief of high pressure in the right atrium, such as the creation of hole(s) in the native or surgically created septum between the left and right atria. These have been designed for the rare conditions of pulmonary hypertension or cavopulmonary connections for certain complex congenital heart diseases.

Accordingly, there exists a need for devices and methods to treat heart failure particularly diastolic and/or systolic failure of the left ventricle and its consequences.

Furthermore, there also still exists a need for devices to relieve high pressure in the left atrium and which will prevent or minimize the chance of the passage of thrombi, especially from the right atrium to the left atrium, and the resulting risk of systemic emboli.

SUMMARY OF INVENTION

It is, therefore, a goal of this invention to effect a reduction in pulmonary venous pressure to ease symptoms of diastolic heart failure. It is a further goal of this invention to create a controlled vent between the left atrium and right atrium to allow a sufficient amount of blood to pass from the left atrium to the right atrium but minimize blood flow from the right atrium to the left atrium.

It is a further goal of this invention to create a controlled vent that will respond to pressure differences between the left and right atrium.

It is a further goal of this invention to provide an interatrial pressure venting device that prevents thrombi from entering the left atrium.

The present invention solves these and other needs by providing a venting device, which in some embodiments comprises a controlled opening or an extended tubular opening, between the left atrium and right atrium that allows an amount of blood to vent from the left heart to the right heart, thereby reducing left atrial pressure and the symptoms associated with diastolic heart failure.

Several unique intracardiac pressure vents, placement catheters, methods of placement and methods of treating heart failure are presented. The intracardiac pressure vents presented allow sufficient flow from the left atrium to the right atrium to relieve elevated left atrial pressure and resulting patient symptoms but also limit the amount of flow from the right atrium to the left atrium to minimize the potential for thrombi or other embolic material from entering the arterial circulation.

In addition, the intracardiac pressure vents presented solve the problem of controlling flow in one direction but minimizing flow in another direction with very low changes in pressure across the device.

Also, the intracardiac pressure vents presented solve the problem of reducing calcium deposition, protein deposition and thrombi formation in a low pressure environment.

Furthermore, the intracardiac pressure vents presented solve the problem of damage to the interatrial septum as well as the rest of the left atrium from excessive pressure against the wall which can cause injury to the tissue and possibly adverse reaction by the patient or compromised function to the interatrial pressure vent.

In addition, atrial arrhythmias are frequently seen in patients with heart failure and may, in part, be caused by chronically elevated left atrial pressure. Therefore, relief of elevated left atrial pressure may lead to reduction of atrial fibrillation.

The present invention provides interatrial pressure vents, placement catheters, methods for placing a device in the interatrial septum within the heart of a patient and methods for treatment of the symptoms of heart failure, particularly diastolic heart failure.

In embodiments, the interatrial pressure vent comprises a body assembly and a flow control element; the body assembly comprises a flexible, substantially open mesh adapted for use in a patient. The flow control element attaches to at least one point of the body assembly and the flow control element provides greater resistance to flow in one direction than it does in another direction.

In embodiments, the interatrial pressure vent comprises a body assembly and a flow control element; the body assembly comprises a flexible, substantially open mesh adapted for use in a patient. The flow control element attaches to at least one point of the body assembly and is at least partially open to flow when there is no pressure differential across the flow control element.

In embodiments, the interatrial pressure vent comprises a body assembly and a flow control element; the body assembly comprises a core segment and at least one flange segment; the flange segment is integral with, or attached to at least one point adjacent to, an end of the core segment; the flange segment extends radially outward from the center longitudinal axis of the core segment. The flow control element attaches to at least one point along the core segment and the flow control element provides greater resistance to flow in one direction than in the opposite direction.

In embodiments, the interatrial pressure vent comprises a body assembly and a flow control element; the body assembly comprises a substantially cylindrical core segment and at least one flange segment; the flange segment is integral with, or attached at least to one point adjacent to, an end of the core segment; the flange segment extending radially outward from the center longitudinal axis of the core segment. The flow control element attaches to at least one point along the core segment and the flow control element provides greater resistance to flow in one direction than another direction.

In embodiments, the interatrial pressure vent comprises a body assembly and a flow control element. The body assembly comprises a substantially cylindrical core segment and at least one flange segment integral with, or attached to at least one end of, the core segment; the flange segment extending radially outward from the axis of the core segment. The flow control element attaches to at least one point along the core segment and the flow control element is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and provides greater resistance to flow in one direction than the other direction.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element extends at least partly onto the flange assembly and creates a sealable contact to the atrial septum and provides greater resistance to flow in one direction than the other direction.

In embodiments, the interatrial pressure vent comprises a body assembly and a flow control element. The body assembly comprises a substantially cylindrical core segment and at least one flange segment integral with, or attached to, at least one end of the core segment and extends away from the axis of the core segment. The flow control element attaches to the flange assembly and creates a sealable connection to the atrial septum and is at least partially open to flow when there is no pressure differential across the flow control element.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element provides greater resistance to flow in one direction than it does in another direction.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element is at least partially open to flow when there is no pressure differential across the flow control element.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments on either side of the core segment being a whole multiple of the number of leaflets.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being a whole multiple of the number of leaflets. The flow control element attaches to at least one point of the body assembly and the flow control element provides greater resistance to flow in one direction than another direction.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being some multiple of the number of leaflets. The flow control element attaches to at least one point of the body assembly and is at least partially open to flow when there is no pressure differential across the flow control element.

In embodiments, an implant system comprises an interatrial pressure vent and placement catheter for treating heart failure. The implant system is comprised of a body assembly and a flow control element. The body assembly is comprised of a substantially cylindrical core segment and at least one flange segment integral with, or attached to, at least one end of the core segment and extending radially away from the core segment. The flow control element is attached to at least one point along the core segment and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube or sheath and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube (or sheath) and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube with at least one flange or circumferential groove formed in the outer diameter and a handle component. The inner shaft also contains at least one lumen that extends along at least part of the length of the inner shaft. The outer shaft comprises an elongate hollow tube (or sheath) and a different handle component that slideably interfaces with the first handle component.

In other embodiments, the invention comprises a device for treating a heart condition in a patient comprising a body element having a core segment defining a passage, a first annular flange comprising a plurality of flange segments, and a second annular flange comprising a plurality of flange segments. In embodiments, at least a portion of one of the flange segments is either more or less flexible than the remaining portion of the flange segment or other portions of the body element, including but not limited to the cylindrical core segment.

In other embodiments, the device comprises a third or intermediate annular flange for better adherence to the septal wall.

In other embodiments, the device comprises a flow control element configured to aim the flow of blood in a desired direction.

In other embodiments, the invention is configured to be more easily retrieved during deployment. Such embodiments can include among other elements at least one extended flange segment in one of the annular flanges that is able to be retained within a placement catheter when the other portions of the device are deployed.

In embodiments, the method of placing the interatrial pressure vent into position may comprise a sequence of steps to locate and gain access to a vascular channel leading to the heart, placing an introducer catheter via this channel into one of the atriums of the heart, locating the interatrial septum between the left and right atriums, creating an opening in the interatrial septum, advancing a placement catheter containing an interatrial pressure vent into one of the atriums and then through the opening created in the interatrial septum between the right and left atriums, and then controllably deploying the interatrial pressure vent so it is securely connected to the interatrial septum.

Deployment of the interatrial pressure vent preferably occurs in a series of steps comprising first advancing the placement catheter through the septal opening, second deploying a first flange, third retracting the placement catheter to position the first flange against the septal wall, and fourth deploying a second flange on the other side of the septal wall from the first flange.

In embodiments where the device disclosed herein is implanted into the atrial septum, the introducer catheter may be placed through the inferior vena cava via a femoral vein to the right atrium.

Other pathways are available including placing the introducer catheter through the superior vena cava via a jugular vein; through the aorta, via a femoral artery, past the aortic valve and into the left atrium; through the aorta, via a brachial artery, past the aortic valve and into the left atrium; through the superior vena cava via a basilica vein; through the superior vena cava via a cephalic vein; intraoperatively, through an opening created in the right atrium either for this reason or during a procedure performed for some other purpose; intraoperatively through an opening created in the left atrium either for this reason or during a procedure performed for some other reason; or via a guidewire that is positioned through the interatrial septum and located in the pulmonary artery.

Regarding the placement catheter, in some embodiments the placement catheter is designed to function as the introducer catheter and the placement catheter, eliminating the need for a catheter exchange. While in other embodiments, the introducer catheter, the placement catheter, or both are constructed to be exchanged over only part of their length to avoid the necessity of handling a guidewire that is at least twice as long as the catheter. Still in other embodiments, the introducer catheter or the placement catheter, or both has a pre-shaped curve to enable orientation of the placement catheter substantially orthogonal to the septal wall. The catheter may be curved between 30° and 45° away from the catheter axis at a point between 5 and 15 centimeters away from the distal end of the placement catheter.

In embodiments of the invention where the inventive device is to be placed in the atrial septum, an opening in the septum can be performed using the introducer catheter in a separate procedure from the interatrial pressure vent placement procedure. Access through the opening can be maintained via a wireguide positioned in the right atrium or the pulmonary artery. The opening can be formed using the placement catheter via a distal tip segment that is part of the placement catheter.

The opening may be predilated using a balloon or other dilating device either as part of the procedure described or as a separate procedure.

In another aspect, the opening is formed and dilated as part of a single, unified procedure with the interatrial pressure vent placement procedure. This may be accomplished by integrating a balloon or other dilating component as part of the placement catheter and dilating the opening as part of placing the interatrial pressure vent. For example, this could be accomplished using a balloon that can be folded to achieve a small loaded profile and will have a suitable pressure capacity and suitable durability to dilate the septum opening and the interatrial pressure vent together.

The opening that is formed in the interatrial septum may be formed by pushing a catheter tip through the septum at the location of septum primum. Because this septum is normally very thin, the distal tip may be pushed directly through without significant force.

In an alternate method, the opening in the interatrial septum can be formed with a cutting tool that is advanced through the introducer catheter or the placement catheter. The tool preferably comprises a blade and a shaft. The blade contains at least two surfaces and one edge. The edge is sharpened and formed at an angle so that the blade slices as it is advanced into and through the septum.

In yet another method, the opening in the interatrial septum can be formed with a cutting tool that is advanced through the introducer catheter or the placement catheter. The tool preferably comprises a blade and a shaft. The blade contains at least two surfaces and two separate edges that are sharpened at an angle so that the blade slices as it is advanced into and through the septum and the septum is cut generally in an x shaped opening.

In yet another method, the opening in the interatrial septum can be formed with a punching tool that is advanced through the introducer catheter or the placement catheter. The punching tool preferably comprises a cutting assembly and a shaft. The cutting assembly preferably comprises a hollow, conical shape with a sharpened edge along the base circumference. The cutting assembly is connected at least to one point on the shaft and is generally oriented so the apex of the cone is pointed away from the shaft.

In one method, the cutting assembly can be operated by advancing the conical assembly through the interatrial septum and then pulling it back to form an opening that is generally circular.

In another method, the cutting assembly can be operated by advancing the conical assembly through the interatrial septum and then rotating it as it is pulled pack to create a circular cutting action against the interatrial septum.

In another embodiment, the cutting tool can be formed of at least one cutting member and one shaft. The cutting member is connected at least to one point along the shaft and the other end of the cutting member is adjustably positioned so it can lay alongside the shaft or at some angle away from the shaft. To place the cutting tool, the cutting member is placed alongside the shaft and then advanced through the septum. Then the cutting member would be adjusted to a second position, radially further away from the shaft than the first position, and the shaft would be positioned so the cutting member exerts lateral stress against the septum. The cutting member could be designed to slice the septum in this manner. In another method, the cutting tool could be rotated once the shaft and cutting member were repositioned so the slicing motion would cut a generally circular hole through the septum.

In embodiments, the cutting member is round wire.

In another embodiment, the cutting member can be connected to one output of a power supply, capable of supplying a suitable signal to the cutting member, the other output of which is connected to a ground plate placed against the patient's skin. An appropriate electric potential can be placed between the cutting member and ground plate to cause a concentrated current density near the wire to aid in cutting through the septum tissue.

In another embodiment, the cutting member is a section of tubing sliced lengthwise and appropriately formed to create a cutting edge. During placement, the cutting member is controllably positioned to lie against the shaft as the shaft is advanced through the placement catheter and through the opening created in the interatrial septum. Once positioned, the placement catheter is retracted and the shaft is positioned within the septum. Once positioned in this manner, the cutting member can be controllably adjusted to a second position, radially further away from the shaft than the first position, and the shaft positioned so the cutting member exerts lateral stress against the septum.

In yet another method, an opening is created in the interatrial septum which is smaller than the diameter of the outer surface of the body of the interatrial pressure vent according to the present invention such that, when the interatrial pressure vent is initially deployed within the interatrial septum, there is some compression from the septum against the body of the interatrial pressure vent.

Referring now to the placement catheter used to position and controllably place the interatrial pressure vent; in one aspect, the placement catheter consists of an inner member and an outer member.

In embodiments, the outer member is comprised of a tubing member and a first handle component, the outer shaft is less than about 16 F in diameter and formed of a material suitably smooth and resilient in order to restrain the stowed interatrial pressure vent and allow smooth stowing and deployment, such as PTFE, FEP, Tefzel, PVDF, HDPE or other suitable materials.

In embodiments, the inner member is comprised of at least one tubing member with an inner lumen through at least part of the tubing member, and a second handle component attached to the proximal end, with the second handle component slideably attached to the first handle component.

In embodiments, the handle components are interconnected via an inclined, helical lever to enable advancement of the inner member relative to the outer member by rotating the outer shaft handle while holding the inner shaft handle.

In embodiments, the handle components comprise a locking mechanism that prevents the handle component from moving in relationship to each other beyond a certain predetermined length In embodiments, the handle components contain at least two locking mechanisms that prevents the handle component from moving in relationship to each other beyond two different predetermined length In embodiments, the inner member contains a stiffening element adjacent to the distal area.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section that has a greater wall thickness than the midsection. The placement device comprises an inner shaft and an outer shaft. The inner shaft comprises an outside diameter and an internal lumen extending at least partly toward the proximal end from the distal end. The outer shaft contains an outside diameter and an inside diameter. The inner shaft contains a necked portion or circumferential groove along at least part of its length of smaller diameter than at least a portion of the inner member distal to the necked portion; the space formed between the outside of the necked portion and the inside of the outer shaft being sufficient to contain a folded or otherwise compressed interatrial pressure vent of the present invention and the space formed between the outside of the non-necked portion and the inside of the outer shaft being insufficient to contain the interatrial pressure vent.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section located radially further away than the midsection and with a larger dimension in the radial direction than the midsection. The placement device comprises an inner shaft and an outer shaft. The inner shaft contains an outside diameter and an internal lumen extending at least partly toward the proximal end from the distal end. The outer shaft contains an outside diameter and an inside diameter. The inner shaft contains a first necked portion or circumferential groove comprising a length and a diameter; the diameter of the first necked portion of the inner shaft being smaller than at least a portion of the inner member distal to the necked portion and the inner shaft also containing a second necked portion, proximal to the first necked portion and of a length sufficient for containing end section of the flange segment and a diameter smaller than the first necked portion; the space formed between the outside of the first necked portion and the inside of the outer shaft being sufficient to contain the folded or otherwise compressed interatrial pressure vent of the present invention except for the end section of the flange segment; the space formed between the outside of the non-necked portion and the inside of the outer shaft being insufficient to contain the interatrial pressure vent and the space formed between the outside of the second necked portion and the inside of the outer shaft being sufficient to contain the end section of the flange segment.

In another aspect, the inner member comprises a first necked portion along at least part of its length of smaller diameter than at least a portion of the inner member distal to the first necked portion and second necked portion, along a second part of its length proximal to the first necked portion and smaller than the first necked portion. The space between the outside of the necked portion and the inside of the outer sheath.

Referring now to the body assembly of the interatrial pressure vent, in one aspect, the body comprises a core segment and at least one flange segment.

In embodiments, the body assembly comprises a core segment; a first flange comprising at least one flange segment at one end of the core segment; and a second flange comprising at least one flange segment at the opposite end from the first flange of the core segment.

In embodiments, the body assembly comprises a core segment, comprising a self expanding mesh; a first flange, at one end of the core segment; and a second flange at the opposite end of the core segment from the first flange.

In embodiments, the body assembly is comprised of a core segment, comprising a balloon expandable mesh; a first flange at one end of the core segment; and a second flange at the opposite end of the core segment from the first flange.

In embodiments, the body assembly is comprised of a core segment; a first flange at one end of the core segment; and a second flange at the opposite end of the core segment from the first flange; each flange oriented to extend substantially radially outward relative to the center axis the flange segment.

In embodiments, the body assembly is comprised of a core segment; a first flange at one end of the core segment; and a second flange at the opposite end of the core segment from the first flange; each flange oriented to extend substantially radially outward from the core segment; and at least one flange extending beyond 90° relative to the center axis of the core segment.

In embodiments, the body assembly is comprised of a core segment; a first flange at one end of the core segment; and a second flange at the opposite end from the first flange of the core segment; each flange oriented to extend substantially radially outward from the core segment; the first flange formed with a smaller radius of curvature than the second flange.

In embodiments the interatrial pressure vent comprises a flow control element biased to allow flow from one atrium of a patient to the other atrium of the patient with lower resistance than in the reverse direction.

In embodiments the interatrial pressure vent comprises a flow control element biased that remains at least partially open when there is no pressure differential across the vent.

In embodiments, the interatrial pressure vent comprises an integral filter to prevent embolic particles larger than about 2 mm from passing beyond the filter in the direction of flow.

In other embodiments, the interatrial pressure vent comprises a tubular flow element which extends a distance beyond the core segment so as to prevent embolic particles from entering the left atrium.

In embodiments, the interatrial pressure vent comprises at least one movable flap that responds to pressure changes between the right and left atrium.

In embodiments, the body assembly may be constructed from preformed wire braid. The wire braid may be formed from nitinol with a martensite/austenite transition temperature is below 37° C. so it remains in its superelastic, austenitic phase during use. The transition temperature is below about 25+/−5° C. The wire should have a diameter of at least about 0.0035 (about 2 lbs of breaking strength at 200 ksi tensile). The wire should have a very smooth surface to reduce thrombogenicity or irritation response from the tissue. The surface finish may be 63 uin RA or better. This surface may be obtained either by mechanical polishing, by electropolishing or a combination. In embodiments, the surface may be cleaned with detergents, acids and/or solvents to remove residual oils or contamination and then controllably passivated to insure minimal corrosion.

In embodiments, the body assembly may be formed from grade 1 titanium. In embodiments, the body may be formed of grade 6 titanium. In embodiments, the body may be formed of grade 9 titanium. In embodiments, the body may be formed of 316L stainless steel. In embodiments, the body may be formed of 416L stainless steel. In embodiments, the body may be formed of nitinol or Elgiloy. In embodiments, the body is formed of platinum iridium. In embodiments, the body may be formed of a cobalt chromium alloy. In embodiments, the body may be formed of MP35N. In embodiments, the body may be formed of Vitalium (TRADEMARK). In embodiments, the body may be formed of Ticonium (TRADEMARK). In embodiments, the body may be formed of Stellite (TRADEMARK). In embodiments, the body may be formed of tantalum. In embodiments, the body may be formed of platinum. Materials disclosed with reference to the body or any component of the device disclosed herein are not meant to be limiting. The skilled artisan will appreciate that other suitable materials may be used for the body or any other component of the device.

In embodiments, the body assembly is preferably formed from a length of cylindrical tubing that is precut with slots at specific locations and then formed in a series of processes to produce a shape suited for the purpose of containing a flow control element within the interatrial septum.

As an example, a first process might be to stretch the cylinder to expand its internal diameter to a uniform target dimension. This can be done with a balloon or a standard tubing expander consisting of a segmented sleeve and tapered conical inserts that increase the diameter of the sleeve when the cones are advanced toward the center. In order that the shape of the stretched tubing be preserved, the cylinder should be annealed while held into this stretched shape by heating it beyond 300° to 600° for at least about 20 minutes to allow the internal stresses to be relieved. A second process might be to form one flange end shape using a similar process as the first process but using a tool shape specially designed for the first flange shape. A third process might be to form the second flange end shape using a similar process as the first process but using a tool specially designed for the third flange shape. These shapes must be annealed using a similar process as the first shape, either in separate steps or altogether.

In embodiments, the internal diameter of the finished interatrial pressure vent is larger than about 5 mm to enable adequate venting of the left atrium and minimize damage to blood components from excessive shear stress, but enabling the interatrial pressure vent to stow in a placement catheter of smaller than about 14 F.

In embodiments, the flow control element opening is at least about 50 sq. mm.

In embodiments, the flow control element opening is 50 sq. mm.+−10 sq. mm.

In another embodiment, the cylindrical section is formed with an inside diameter of between 3 and 15 mm.

The internal diameter of the body segment is preferably a constant dimension along the center, longitudinal axis of the interatrial pressure vent and is long enough to isolate the flow control element from deflection or damage as a result of contact with other structural elements of the heart.

In embodiments, the body segment is formed into a substantially toroidal shape, the inner diameter tapering down and then up again from one side of the implant to the other.

In embodiments, the length of the body section may be about 4 mm.

In embodiments, the length of the body section may be between about 3 mm and about 40 mm.

In yet other embodiments, the flange segment may comprise at least a single loop which is oriented to the cylindrical shape by at least about 90° relative to the central axis of the cylinder and projected outward to a distance away from the center axis of greater than the opening in the atrial septum but at least about 3 mm further than the diameter of the inner cylinder.

In embodiments, the flange segment is formed of multiple struts that extend radially outward, with respect to the center aspect of the cylinder.

In embodiments, the flange struts each comprise a substantially triangular shape that is wider adjacent to the body section than at the outer edge of the strut.

In embodiments, the flange struts comprise a substantially triangular shape that is wider adjacent to the body section than at the outer edge of the strut and contains an integral hole at the outer edge for containing a radiopaque marker.

In embodiments, the flange struts comprise a substantially triangular shape that is wider adjacent to the body section than at the outer edge of the strut and whose outer edge is rounded to reduce trauma against the tissue it contacts.

In embodiments, the flange struts are formed from a single beam of material that project outward from the center longitudinal axis of the body section.

In embodiments, the flange segment is formed of spiral shaped flange struts that are coplanar and substantially orthogonal to the central axis of the cylinder.

In embodiments, the flange segment is formed of at least one looping member that attaches to at least one portion of the body section.

In embodiments, the flange is preferably formed to automatically recover substantially to its preformed shape following partial deployment of the interatrial pressure vent from the placement catheter. In this manner, the interatrial pressure vent will resist being pulled back through the septal opening.

In embodiments, the flow control element device may be a tissue valve, a synthetic valve or a combination. The flow control element can be formed from animal or human tissue, such as bovine pericardial tissue. The procedures for obtaining these tissues and preparing them for use as implanted valve components are well known to those skilled in the art. The flow control element could be a trileaflet valve, or also a bileaflet valve, or also a simple flap valve. The flow control element could also be a ball and socket valve, a duckbill valve, a butterfly valve, or any other valve component known to those skilled in the art.

In embodiments, the flow control element can be biased by adding a separate component that is attached to at least one point along the body or flange segment and contacts against at least one point of the flow control element surface at least at some point during its duty cycle. The component can be preformed to controllably affect the flow control element behavior. For example, in one embodiment, the flange segment can be a looped wire formed from nitinol and connected to the body section and cantilevered against the surface of the flow control element facing the left atrium and formed so that the surface of the flow control element is biased to be slightly open when the pressure is equal in the left atrium and right atrium. Biasing can also be accomplished by varying the stiffness of the material of the valve or components thereof.

In embodiments, a flange segment could be formed out of a helical winding of nitinol, with a core wire to connect one end of the flange segment to the other end.

In embodiments, the flow control element can be preshaped to resist moving against pressure in one direction.

In embodiments, the flow control element could be biased to remain open at a predetermined pressure, or at a neutral pressure.

In embodiments, the interatrial pressure vent consists of a body section and a flow control element; the body section comprising a cylindrical core segment and two flanged end sections; the flow control element being sealably secured to at least three points along the body section; the flanged end sections each comprising at least one flange segment that extends radially outward from the body section; the flow control element comprising at least one movable element that allows fluid passage in one direction with lower resistance than another direction.

In embodiments, the body section is elliptical in shape, or cylindriod and designed to offset asymmetric stress created by a linear septal opening.

In embodiments, the formed metal flange segments consist of at least two flange segments, with at least one on each side of the septum.

In embodiments, the flange segments are positioned so they do not pinch the septum between them, thereby reducing possible pressure necrosis.

In embodiments, the flange segments are shaped so the wall thickness perpendicular to the septum is less than the wall thickness parallel to the septum, thereby increasing flexibility without decreasing strength.

In embodiments, the flange segments are formed so the radius of curvature at the end is greater than about 0.03 inches.

In embodiments, there is a radiopaque marker, preferably tantalum or platinum alloy, formed around, or integral with, the flange segment end to increase radiopacity and increase the area of contact between the flange segment and septum.

In embodiments, the flange on the left atrium side of the septum is bent at a shorter radius of curvature than the right atrium side.

In embodiments, the flange on one side of the interatrial septum is formed to return to greater than a 90° angle relative to the axis of the center cylinder.

In embodiments, holes are preformed at a location along the cylindrical section for suture sites for securing the valving device.

The above summary of the invention is not meant to be exhaustive. Other variations and embodiments will become apparent from the description and/or accompanying figures disclosed herein and below. The embodiments described above employ elements of each other and are meant to be combined with each other. For example, embodiments of flow control element may be used with differing configurations of the body element, flange, or segment thereof. While certain combinations are disclosed, the invention is not so limited

BRIEF DESCRIPTION OF DRAWINGS

The present invention will become more fully apparent from the following description and appended claims, taken in conjunction with the accompanying figures. Understanding that these figures merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying figures in which:

FIG. 4 is perspective view of the body assembly of the interatrial pressure vent by itself;

FIG. 5 is a right side view of the body assembly of FIG. 4;

FIG. 6 is a distal end view of the body assembly of FIG. 4;

FIG. 7 is an enlarged fragmentary cross-sectional view taken along line 7-7 of FIG. 6;

FIGS. 7A through 7C are a side elevational views of embodiments of the device in the stowed position;

FIG. 8 is a side elevational view of the interatrial pressure vent of FIG. 1 in a collapsed configuration prior to loading in a placement catheter;

FIG. 9 is a side view of the distal end of a placement catheter in its open position;

FIG. 10 is a side view of the distal end of a placement catheter in its open position and with an interatrial pressure vent in its stowed configuration and in position over the inner shaft of the catheter;

FIG. 11 is a side view of the distal end of a placement catheter in a closed configuration with an interatrial pressure vent in its stowed configuration loaded onto the placement catheter;

DETAILED DESCRIPTION OF INVENTION

Figure 1:
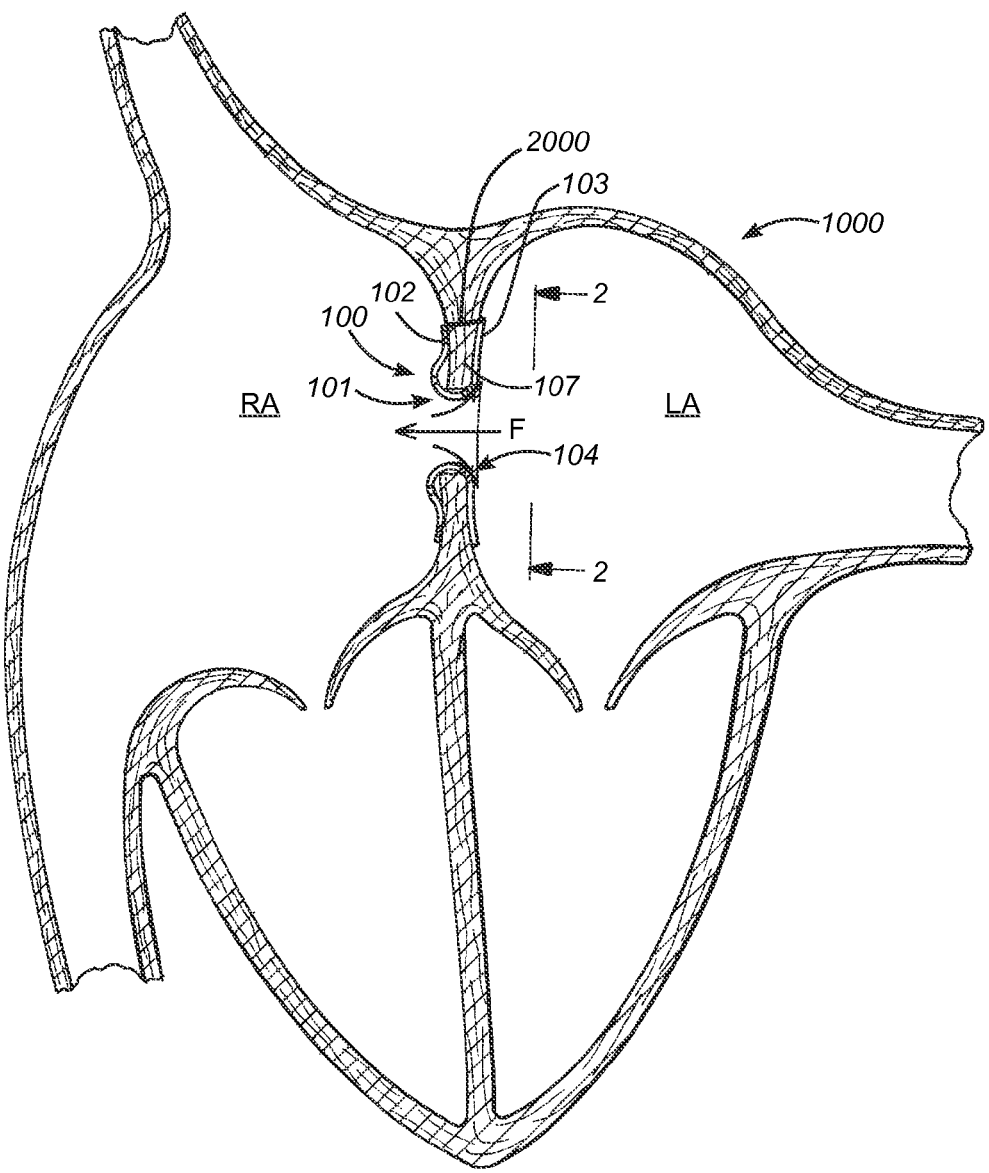
FIG. 1 is a schematic cross-sectional view of a patient's heart with an interatrial pressure vent of the present invention in situ.

Certain specific details are set forth in the following description and Figures to provide an understanding of various embodiments of the invention. Those of ordinary skill in the relevant art will understand that they can practice other embodiments of the invention without one or more of the details described below. Finally, while various processes are described with reference to steps and sequences in the following disclosure the steps and sequences of steps should not be taken as required to practice all embodiments of invention.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring treatment for symptoms of heart failure.

As used herein, the term "pressure differential" means the difference in pressure between two points or selected spaces; for example between one side of a flow control element and another side of the flow control element.

As used herein, the term "embolic particle" means any solid, semi-solid, or undissolved material, that can be carried by the blood and cause disruption to blood flow when impacted in small blood vessels, including thrombi.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at some angle greater than 0 relative to the center longitudinal axis of the cylinder.

As used herein, the term "axial thickness" means the thickness along an axis parallel to the center longitudinal axis of a shape or component.

As used herein, the term "axial direction" means direction parallel to the center longitudinal axis of a shape or component.

As used herein, a "sealable connection" is an area where components and/or objects meet wherein the connection defines provides for an insubstantial leakage of fluid or blood through the subject area.

As used herein, the term "lumen" means a canal, duct, generally tubular space or cavity in the body of a subject, including veins, arteries, blood vessels, capillaries, intestines, and the like.

As used herein, the term "sealably secured" or "sealably connected" means stably interfaced in a manner that is substantially resistant to movement and provides resistance to the flow of fluid through or around the interface.

As used herein, the term "whole multiple" means the product contains no decimal.

The present invention provides structures that enable several unique intracardiac and intraluminal valve devices and placement catheters therefor. In some embodiments directed toward the intra-cardiac setting, these valve devices are intended to allow sufficient flow from the left atrium to the right atrium to relieve elevated left atrial pressure and resulting patient symptoms but also prevent the amount of flow from the right atrium to the left atrium to minimize the potential for thrombi or other embolic material from entering the arterial circulation.

However, it should be appreciated that the invention is applicable for use in other parts of the anatomy or for other indications. For instance, a device such as that described in this disclosure could be placed between the coronary sinus and the left atrium for the same indication. Also, a pressure vent such as is described in this disclosure could be placed between the azygous vein and the pulmonary vein for the same indication.

Referring now to FIG. 1, one embodiment of invention is shown where the invention is used as an interatrial pressure vent. FIG. 1 depicts the heart of a human subject. "LA" refers to the left atrium, and "RA" refers to the right atrium. The interatrial septum is depicted as 107. Interatrial pressure vent 100 includes a body element 101 and flow control element 104, embodiments of which will be described in further detail below. The body element 101 comprises flanges 102 and 103. In this and other embodiments described herein, flanges 102 and 103 may be annular flanges, which define a gap 2000 into which the septum 107 fits. In embodiments, after insertion, the interatrial pressure vent is securely situated in an opening created in the interatrial septum. Arrow F in FIG. 1 shows the direction of flow. It can be thus seen that a build up of pressure in the LA can be vented, by way of the inventive device, to the RA.

Figure 2:
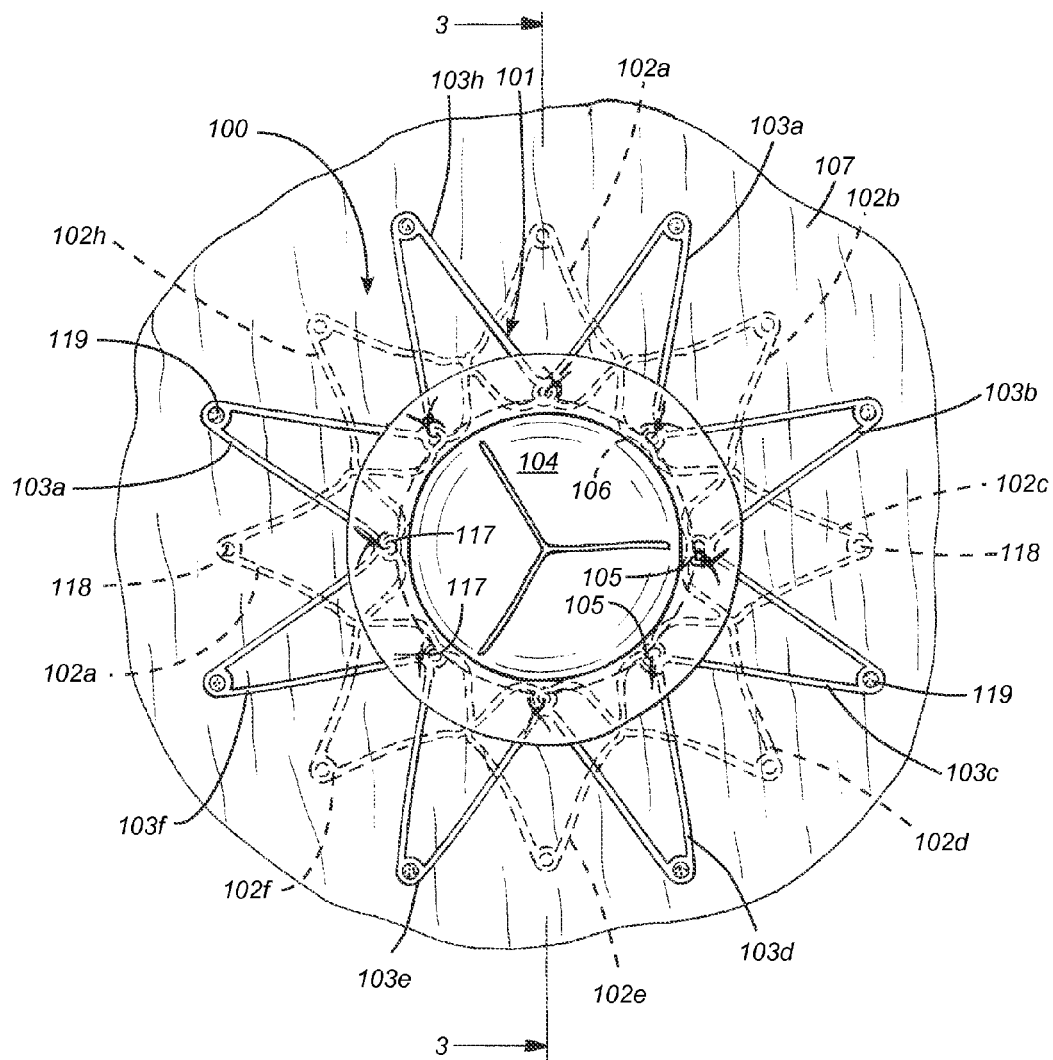
FIG. 2 is an end view of the interatrial pressure vent of FIG. 1 in situ as seen along line 2-2 of FIG. 1.

Referring now to FIG. 2, an embodiment of the interatrial pressure vent of the present invention is illustrated. Interatrial pressure vent 100 includes body element 101 comprising a substantially open mesh and including a substantially cylindrical core segment (shown end on) 106 and substantially annular flanges 102 and 103. Flanges 102 and 103 may be comprised of any number of flange segments (or "flange elements" or "flange members") 102a-102h and 103a-103h, that are attached adjacent to the end of the core segment and extend radially outward from longitudinal axis of the core segment and flow control element 104. "Flange segments" may also be referred to as "legs" herein. The flanges 102 and 103 (and thus the segments which comprise them 102a-h and 103a-h) in this and all embodiments disclosed herein, may also be integral with the core segment. That is, they need not be necessarily "attached" thereto but may be fabricated from the same material that defines the core segment (including in the manners described above and herein) and thus may be contiguous therewith. The flow control element may be attached to the body element, for example at locations 105. The flange segments in this and any embodiment of any annular flange may be formed of two individual strut elements or also can be formed of a single element. The flange segments may be generally rectangular in cross section, circular in cross section, oval in cross section or some other geometric shape.

Figure 2A:
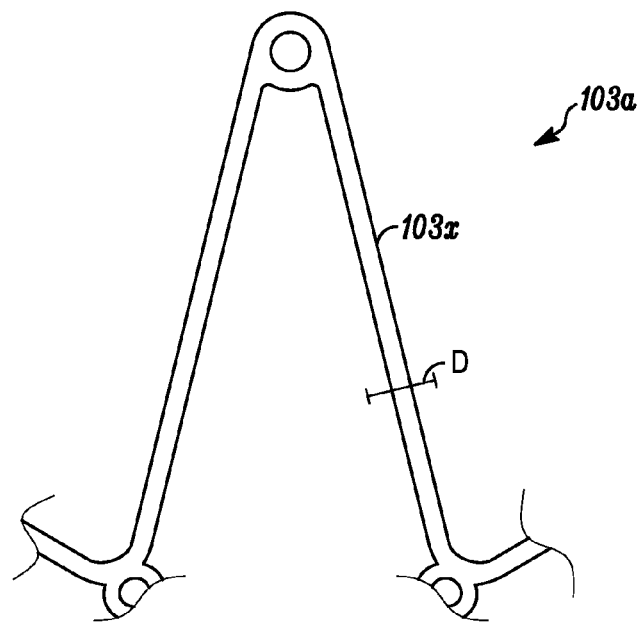
FIG. 2A is an end-on close up view of a flange segment of an embodiment of the present invention.
Figure 2B:
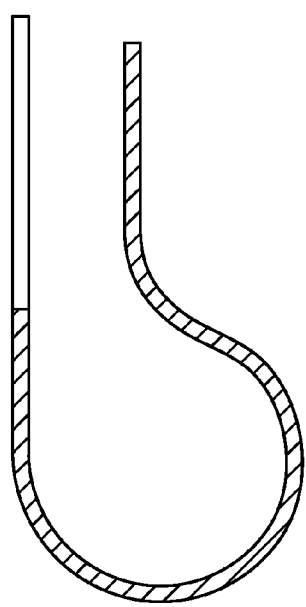
FIG. 2B is an enlarged side cross-sectional view of an embodiment of the invention to illustrate variations in flexibility in a flange.

In embodiments, the flange segments are designed to be more flexible than the core segment. In such embodiments, the increased flexibility may be achieved in several ways. In embodiments, a dimension of the surface of the strut elements that make up the flange segments is altered relative to the corresponding dimension of the struts (or elements, or members) that make up the core segments. FIG. 2A illustrate such embodiments. FIG. 2A shows an example flange segment 103a viewed end on. As shown, the end-facing dimension of strut element of 103x has a width D. By decreasing the width D in relation to the width of the outward-facing dimension of the struts that comprise the core segment, an increased flexibility of the flanges in relation to the core segment or other flange members (or portions thereof) can be achieved. FIG. 2B shows an enlarged fragmentary cross-sectional of an embodiment of the device substantially shown in FIG. 6. The view is taken along line 7-7 of FIG. 6. In this figure, the cross hatched area shows the area of increased flexibility. It can be seen that one area of the flange segment is thus more flexible than another area. In embodiments where the strut elements are circular, then in a similar fashion, the diameter of the strut element could be made to have a diameters less than the diameter of the strut (or similar elements) comprising the mesh-like configuration of the core segment. In embodiments where the flange element is made from a different section of material and is attached to the core segment, the segment material could be chosen to have a greater flexibility than the core segment (or remaining portion of the flange segment or flange itself as the case may be). The choice of materials based on their flexibility will be apparent to those skilled in the art. In the ways described above, the flange segments can achieve greater flexibility than the core segment (or the remaining portion of the flange segment or the flange itself as the case may be) thereby reducing probability of damage to the tissue of the septum while allowing the core segment to maintain a strong outward force against the septal opening and thus decrease the probability that the device could become dislodged.

In embodiments having an open-mesh configuration for the body element 101, the body element can be formed from a number of materials suitable for use in a patient, such as titanium, nitinol, stainless steel, Elgiloy, mp34n, Vitalium, Mobilium, Ticonium, Platinore, Stellite, tantalum, platinum, or other resilient material. Alternatively, in such embodiments, the body element 101 can be formed from a polymer such as PTFE, UHMPE, HDPE, polypropylene, polysulfone, or other biocompatible plastic. The surface finish of the body element may be smooth with no edges or sharp discontinuities. In other embodiments, the surface finish is textured to induce tissue response and tissue ingrowth for improved stabilization. In embodiments, the open mesh of body element 101 can be fabricated from a resorbable polymer such as polylactic acid, polyglycolic acid, polycaprolactone, a combination of two or more of these or a variety of other resorbable polymers that are well known to those skilled in the art.

In embodiments, the structure of the body element may be uniform and monolithic.

In other embodiments, the body element (mesh or monolithic) comprises porous materials to encourage tissue ingrowth or to act as a reservoir for containing one or more compounds that will be released over time after implant to address numerous issues associated with the product performance. These compounds can be used to diminish calcification, protein deposition, thrombus formation, or a combination of some or all of these conditions. The compound can also be used to stimulate an irritation response to induce tissue ingrowth. In embodiments, the compound can be an anti-inflammatory agent to discourage tissue proliferation adjacent to the device. Numerous agents are available for all of such uses and are familiar to those who are skilled in the art.

In embodiments, the material that comprises the body may be multilayered comprising a coating of resorbable polymer or semipermeable polymer that may comprise various compounds that may be released, and in some embodiments in a controlled manner over time, after implant to address numerous issues associated with product performance.

The mesh can be formed from wire that is pre-bent into the desired shape and then bonded together to connect the component elements either by welding them or adhesively bonding them. They could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

In other embodiments, the mesh can be formed from a hollow tube that has been slotted using, for example, a machining laser or water drill or other method and then expanded to form the open structure. If a sufficiently elastic and resilient material, such as nitinol, is used, the structure can be preformed into the finished shape and then elastically deformed and stowed during delivery so the shape will be elastically recovered after deployment. The surface of the finished assembly must be carefully prepared to insure is passivated and free of surface imperfections that could be nidus for thrombus formation.

In embodiments, the flow control element 104 is a tissue valve such as a tricuspid valve, a bicuspid valve or a single flap valve formed from pericardial tissue from a bovine, porcine, ovine or other animal. Any number of cusps may be used. The flow control element is formed using a number of processing steps and auxiliary materials such as are well known in the art.

The flow control element 104 can also be a ball valve, a duckbill valve, a leaflet valve, a flap valve, a disc in cage type valve, a ball in cage type valve or other type of valve formed from a polymer or polymers or a combination of polymers, ceramics and metals such as dacron, teflon, polyurethane, PET or other suitable polymer; titanium, stainless steel, nitinol, MP35N, elgiloy, or other suitable metal; zirconia, silicone nitride, or other suitable ceramic. Valves or portions thereof may comprise different stiffness/flexibly properties with respect to other valves or portions thereof in the flow control element.

The flow control element 104 preferably extends to a point along the flange assembly 103 to enable creation of a sealable connection to the septum wall after placement. This is more particularly shown in FIG. 3 where it can be seen that in embodiments, the flow control element extends beyond the length of the core segment and is folded and attached to the core segment so as to create a lip that extends in a direction center of the opening in the vent. When the device is abutted against the septal wall, this lip forms said sealable connection and thus can reduce the likelihood that blood can flow through the septal opening via pathways between the outer surface (septal-facing surface) of the interatrial pressure venting device and the septal opening. The flow control element 104 is attached to the body element 101. This can be accomplished by using a suture material, such as silk, nylon, polypropylene, polyester, polybutylester or other materials such as are well known to those skilled in the art. In embodiments, flow control element 104 can be attached to body element 101 using adhesive bonding agents such as cyanoacrylate, polymethylmethacrylate, or other materials such as are well known to those skilled in the art. In other embodiments, flow control element 104 can be attached to body element 101 via staples, rivets, rings, clamps or other similar methods as are well known to those skilled in the art.

As mentioned above, flow control element can be made of material selected for its flexibility/stiffness. In embodiments where a loose valve is desired that resonates more closely with the cycle of the heart, a however stiffness material may be chosen. In embodiments where it is desired to open the valve when the pressure differential reaches a selected value, the material of the flow control element can be selected and/or processed in a manner to open at the desired differential. The leaflets or sections of the flow control element itself may also comprise areas of variable stiffness, and or may be more flexible or less flexible than other leaflets or components of the flow control element.

Figure 3:
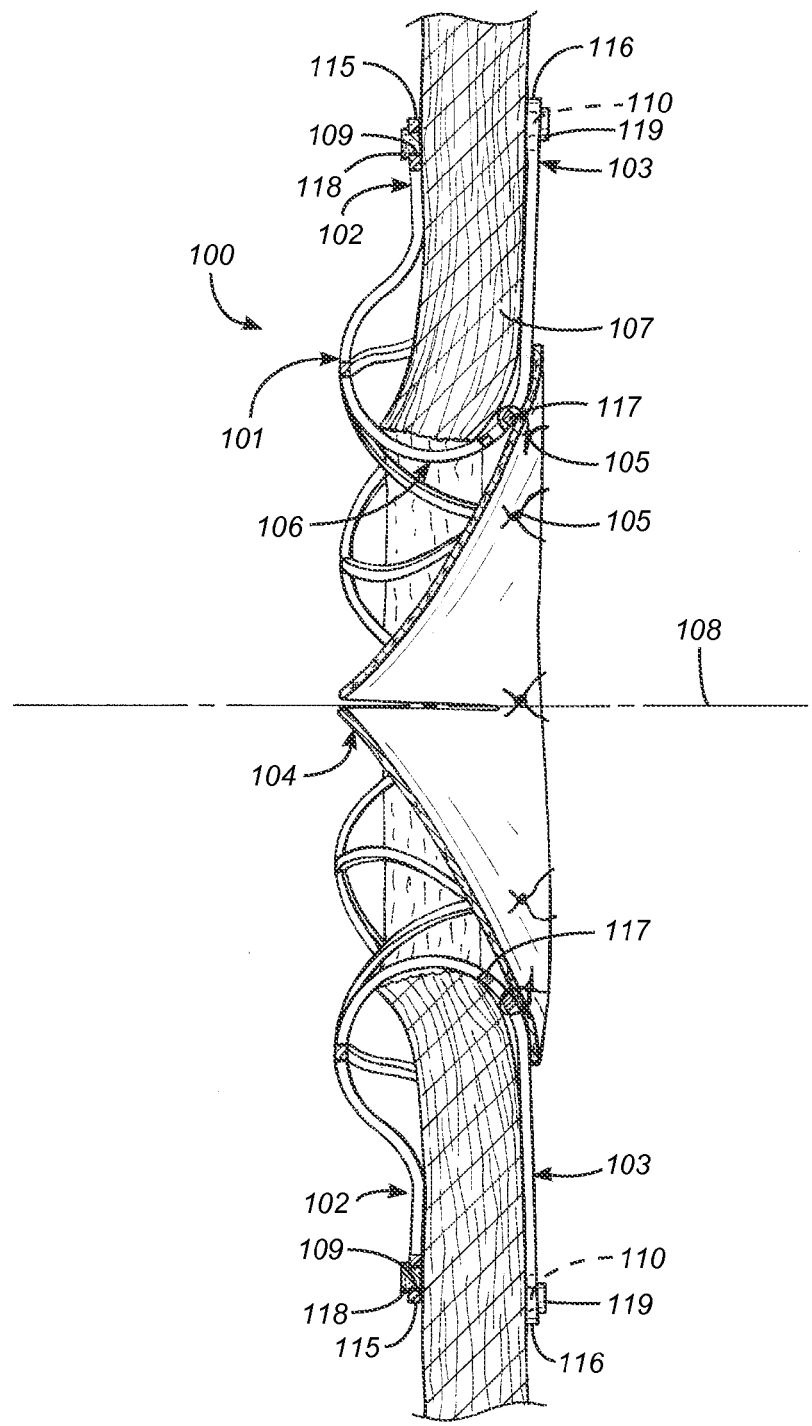
FIG. 3 is a cross-sectional side view taken along line 3-3 of FIG. 2.

FIG. 3 shows the device implanted in the atrial septum of the heart of a patient. As can be seen from the figure, the core segment 106 can be formed contiguously with flanges 102 and 103 and thus flange segments 102a-102h and 103a-103h respectively. In the embodiment shown, flow control element 104 is contained within the core segment 106 so it does not extend beyond the face of the body element 101, thereby insulating it from contact from other body structures or peripheral tissue. in embodiments, the core segment 106 can be extended to protrude beyond the interatrial septum 107 and the flange assembly 102 and/or 103 on at least one side of the interatrial septum 107 and can be formed with a shape that extends to create a lip in the manner described above. In embodiments, the ends of the flange assemblies 102, 103 are formed to lie at a parallel angle to and against the septal wall along at least a part of its length to increase the area of contact and thereby decrease the stress concentration against the septal wall.

Referring now to FIG. 4, an embodiment of the body element of the present invention is shown. This perspective view of the body element 101 shows how, in embodiments, the ends of flange segments 102a-102h, 103a-103h are rounded at their distal ends 115 and 116 to reduce stress concentrations against the interatrial septum after placement. This rounded shape can easily be formed as part of the integral shape of the flange segment. In other embodiments, the thickness of the segment in this area may be decreased to decrease the stress further against the interatrial septum, which is similar to embodiments described above. Also similar to embodiments described above, if the segment is round, the diameter can be decreased in order to increase flexibility. Also, as described above a different material of higher flexibility could be used for the end portions of the segments.

Figure 7B:
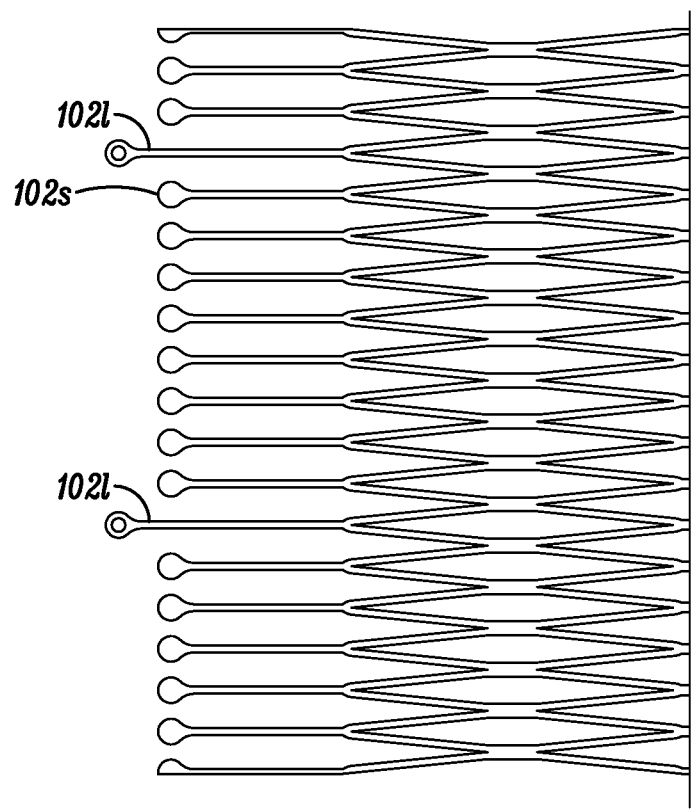
Figure 7C:
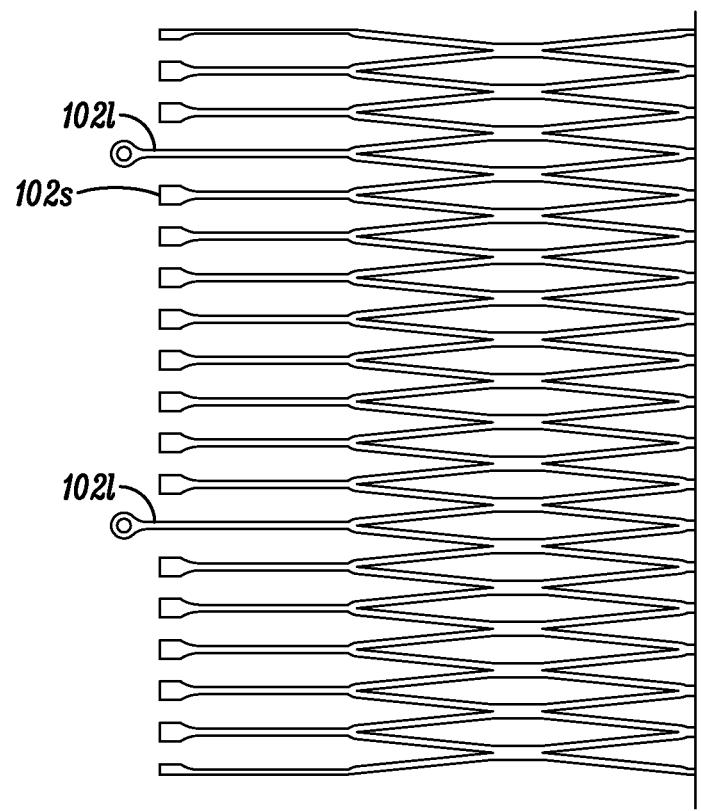

While rounded shapes at the ends of the flange segments reduce stress on the septum, other variations on this theme are contemplated. FIGS. 7A through 7C illustrate embodiments where the shape of the end portions of the flange segments has configurations to achieve less stress against the septal wall—among other goals. FIG. 7A is a side elevational view of embodiment of the pressure venting device in its stowed configuration. Core segment 106 of body element 101 is shown and, in this embodiment, is integral with flanges 103 and 102. The individual flange segments are not labeled; however, it is easily seen that flange 103 comprises segments substantial similar to those described above. There is no eyelet or opening at the end of the segment in the embodiment shown. Flange 102 shows an embodiment where the flange segment is not comprised of a triangular or multi-strut arrangement as described above but rather a single-member segment. Any flange of the present invention may be constructed with single-member segment. An example single member is referred to as 103s. In this example, at the end of each single-member flange segment (102s) for example, there is an eyelet. FIG. 7B shows an embodiment similar to that shown in FIG. 7A where the end of the segments 102s are not eyelets but rather pads. FIG. 7C shows another embodiment where the ends of the segments 102 are paddle shaped. Other smooth-edged shapes could be used, and it should be understood that such shapes and configurations apply to all manner of flange segment ends, not only single-member segments. This would include the ends of flange segments shown and described herein, for example with reference to FIGS. 2 through 7.

FIGS. 7A-C also show embodiments having at least one flange segment being longer than the other flange segments. Again, while represented as single-member flange segments they need not be and as such a configuration with at least one longer segment may apply to any flange-segment configuration disclosed herein. The benefits and purpose of having at least one longer flange segment will be described more fully below.

In embodiments, the outer ends of the flange segments 102a-102h, 103a-103h are formed with integral marker holes or slots 109 and 110 (shown in FIGS. 3 and 7 for example) in which markers 118 and 119 can be positioned so the device may more easily be visualized using radiographic imaging equipment such as with x-ray, magnetic resonance, ultrasound or other imaging techniques. Markers as disclosed herein may be applied to the ends of any segments, not just those with holes or eyelets therein. A radiopaque marker 118 and 119 can be swaged, riveted, or otherwise placed and secured in the hole and thereby dimensioned to be flush with the end of the segment. Markers may also be simply attached or to end of a segment not having a hole. In all embodiments having markers, flange ends 115 and 116 are more visible when imaged. In other embodiments, the markers 118 and 119 can be bonded with an adhesive agent such as cyanoacrylate or epoxy or a variety of other materials that are available and suitable for implant as are well known. The markers may be proud (as shown for example in FIG. 7) or flush with the end of the flange segment. The radiopaque marker 118 and 119 may be formed of tantalum, tungsten, platinum irridium, gold, and alloys of these materials or other materials that are known to those skilled in the art. Also markers 118 and 119 comprising cobalt, fluorine or numerous other paramagnetic materials or other MR visible materials that are known to those skilled in the arts can be incorporated together with the radiopaque materials, or in alternating locations of the flange segments to enable both x-ray and MR imaging of the interatrial pressure vent. Alternatively, the ends of the flange elements 102a-102h and 103a-103h can be wrapped with a foil made of the same marker materials. In embodiments, the radiopaque material can be laminated to the flange segments and bonded through a welding process or using an adhesive such as cyanoacrylate or numerous other adhesives known to those skilled in the art.

Suture rings 117 can be formed in the body element to locate and fix the attachment site along the body element to the flow control element. The suture rings can be circular holes formed into the structure or they could also be some other shape such as rectangular or triangular and also can be formed as a secondary step, for example by standard machining techniques, using a secondary laser machining step, or with electro-chemical etching. Preferably the connection between a segment and any other segment of the body element are formed with as large a radius as possible to increase resistance to fatigue failure. Also, preferably, all edges of the formed device are rounded to improve biocompatibility and hemocompatibility.

The pattern of suture rings as well as which of the rings are selected during suturing may affect the properties of the flow control element. For example, in embodiments where it is desired to have the flow element loose and flappable, less suture rings may be utilized and, in such embodiments, RA-side end of the flow control element may contain relatively less sutures than the LA side. In other embodiments, it may be desirable to keep the flow control element affixed to the core segment for an increased length of the segment thereby reducing the amount of flow control element material that affecting flow. Still in other embodiments the top or bottom portion the flow element at the RA side may be sutured in such a way so as to allow the top or bottom portion of the flow control element to affect flow more than the other portion respectively. Embodiments discussed below where the flow is "aimed" may utilize suturing patterns effective to enable the desired flow control element configuration.

Returning to the flange segments, in an embodiment, the interatrial pressure vent 100 is comprised of an equal number of flange segments on each side of the interatrial septum. In embodiments, there are eight flange segments on each side of the core segment. In another aspect there are an equal number of suture rings and flange segments on one side of the interatrial pressure vent. In other embodiments, there are seven flange segments on each side of the core segment. In other embodiments, there are six flange segments on each side of the core segment. In other embodiments, there are five flange segments on each side of the core segment. In other embodiments there are four flange segments on each side of the core segment. In other embodiments there are three flanges on each side of the core segment. In other embodiments there are two flanges on each side of the core segment. In other embodiments, there is one flange on each side of the core segment. Still in other embodiments there are more flange segments as compared to flange segments. And in other embodiments, there are more flange segments as compared to flange segments. As can be seen there are a number of variations for the number of flange segments and the skilled artisan will appreciate that any number could be used while not deviating from the scope and spirit of the invention.

Referring now to FIG. 5, the body element of an embodiment of the present invention is displayed in side view. The flange segments can be formed to produce a gap G (also referred to as an annular gap) between the ends of flange segments on one side of the body and flange segments on the other side of the body, when the device is in its "native" or un-deployed state. When the device is deployed, it flexes to accommodate the tissue and as such the gap may expand when tissue is positioned therein. In embodiments, this gap is slightly smaller than the thickness of the interatrial septum. In other embodiments, the gap can be larger than the thickness of the interatrial septum. In other embodiments the gap can be zero. In another aspect the gap can be negative: in this case the flange segments on each side of the body can be formed to cross each other in order to exert more pressure between the deployed flange segments and the interatrial septum. Also shown in FIG. 5 are radiopaque markers 118 and 119, which in embodiments are shown to be located adjacent to the end of the flange segments.

Referring now to the embodiment shown in FIG. 6, the flange segments 102*a*-102*h* are oriented so they are not directly opposed to flange segments 103*a*-103*h* on the opposite side of the body element so that after placement there is no pinching points thereby reducing the chance for tissue injury. In embodiments, flange segments 102*a*-102*h* are arranged midway between adjacent ends of flange segments 103*a*-103*h*. In embodiments the length of flange segments 102*a*-102*h* are similar to the length of flange segments 103*a*-103*h*. However in other embodiments the length of flange segments 102*a*-102*h* are identical to the length of flange segments 103*a*-103*h*; the length of flange segments 102*a*-102*h* are longer than 103*a*-103*h*; and the length of flange segments 102*a*-102*h* are shorter than flange segments 103*a*-103*h*.

Referring now to FIG. 7, in embodiments having radiopaque markers it can be seen that the radiopaque markers 118 and 119 may be placed into the marker holes 109 and 110 (or placed on the ends of flange segments that do not have holes) to locate the ends of the flange segments 102*a*-102*h* and 103*a*-103*h* with a non-invasive imaging technique such as with x-ray or MRI during or after the procedure. In embodiments, the markers 118 and 119 can be formed to be flush in an axial direction with the outer surface and the inner surface of the flange segments 102*a*-102*h* and 103*a*-103*h*. In another aspect, the markers 118 and 119 can be formed to extend in an axial direction beyond the outer surface of the flange segments 102*a*-102*h* and 103*a*-103*h*, away from the interatrial septum. In embodiments, the markers 118 and 119 can be formed to extend in an axial direction beyond the inside of the flange segments 102*a*-102*h* and 103*a*-103*h*, toward the interatrial septum. In embodiments, the markers 118 and 119 can be formed to extend in an axial direction beyond the inside and the outside of the flange segments 102*a*-102*h* and 103*a*-103*h*. In embodiments, the markers 118 and 119 can be formed to be recessed in an axial direction within the surface of the inside of the flange segments 102*a*-102*h* and 103*a*-103*h*. In embodiments, the markers 118 and 119 can be formed to be recessed in an axial direction within the outside of the flange segments 102*a*-102*h* and 103*a*-103*h*. In embodiments, the markers 118 and 119 can be formed to be recessed in an axial direction within both the inside and the outside of the flange segments 102*a*-102*h* and 103*a*-103*h*. In embodiments, the markers 118 and 119 can be formed to extend in a radial direction within the width of the flange segments 102*a*-102*h* and 103*a*-103*h*. In embodiments, the markers 118 and 119 can be formed to extend in a radial direction flush with the width of the flange segments 102*a*-102*h* and 103*a*-103*h*.

Referring now to FIG. 8, an interatrial pressure vent 100 of the present invention is shown in its stowed configuration. In embodiments, the interatrial pressure vent can be collapsed to a substantially cylindrical shape for stowing in a delivery catheter during placement. Flange segments 102*a*-102*h* and 103*a*-103*h* can be fabricated to be substantially equal in length. The "stowed position" is not meant to apply only to devices having flange segments of equal length but rather to all embodiments of the venting device disclosed herein. Devices having flange segments of varying length and orientation such as those described herein are also designed to stow in substantially the same manner as shown in FIG. 8. In an embodiment 200 seen in FIG. 20, flange segments 202*a*-202*h* and 203*a*-203*h* are formed on a slanted angle so that, when marker elements are secured to the ends of the flange segments, the flange segments can be stowed into a smaller volume. In embodiments 300 seen in FIG. 21, flange segments 302*a*-302*h* are formed of alternating length to allow stowage into a smaller volume.

Referring now to FIG. 9, an embodiment of the distal end of the placement catheter 111 of the present invention is shown in its open position. The inner shaft 112 is fabricated with a center lumen 136 of sufficient diameter to contain a guidewire 138 or also for use in injecting contrast or other liquid. Commonly, the lumen would be sized for a guidewire of 0.010", 0.011", 0.014", 0.018", 0.021", 0.028", 0.035", 0.038", 0.042" or 0.045". This lumen 136 can also be used to measure pressure at the distal end of the catheter using other equipment and techniques that are well known to those skilled in the art. The lumen 136 preferably extends through the entire length of the inner shaft 112. Alternatively, the guidewire lumen 136 can extend for a shorter length in the proximal direction and then through a side hole (not shown) of the inner sheath. A corresponding side hole (not shown) is placed on the outer shaft 113 adjacent to the side hole in the inner shaft 112 to create a pathway between the center lumen 136 of the inner shaft 112 and the outside of the outer shaft 113. In this way it is possible to pass a guidewire from this distal end of the inner lumen 136 through the side hole and exchange the catheter over a guidewire that is less than twice the length of the catheter 111 while securing the guidewire position during exchange.

In embodiments, the inner shaft 112 is configured with a waist section 120 to contain the folded interatrial pressure vent 100 between the gap formed in the space outside of this section of inner shaft 112 and the inside of the outer shaft 113. The inner shaft 112 is may be formed to contain at least one circumferential groove 114 at the proximal end of waist section 120 that forms a recess between the inside of the outer shaft 113 and the smallest diameter of the groove that is greater than the gap formed in the space between the waist section 120 and the inside of the outer shaft 113. Radiopaque markers 118 can extend in a radial direction past the outer surface of the flange segments 102a-102h and in embodiments, when interatrial pressure vents of the present invention are is folded into their stowed configuration and placed into position over inner shaft 112, radiopaque markers 118 are dimensioned to fit into groove 114. Other similarly dimensioned sections may be used; that is, that which fits into the groove need not necessarily be a radiopaque marker. In embodiments, when interatrial pressure vents of the present invention are stowed in this manner, the gap between waist section 120 and the inside of outer shaft 113 is not sufficient to allow radiopaque markers 118 beyond the distal end of groove 114 unless the outer sheath 113 is retracted beyond the proximal end of groove 114.

The inner shaft 112 may be formed with a groove 121 on the distal end of the waist section 120 adjacent to the location of the distal end of the interatrial pressure vents of the present invention are radiopaque markers 119 (or similar dimensioned members) can extend in a radial direction past the outer surface of the flange segments 102a-102h and in embodiments, when interatrial pressure vents of the present invention are folded into its stowed configuration and placed into position over inner shaft 112, radiopaque markers 119 are dimensioned to fit into groove 121. In another aspect, the inner shaft 112 may be formed with a circumferential groove 114 on the proximal end of waist section 120 and a circumferential groove 121 on the distal end of the waist section 120 The inner shaft can be formed of a variety of polymers or metals or combinations of polymers and metals that are suitable for use in a patient. The inner shaft can be fabricated from a single length of PTFE, UHMWPE, FEP, HDPE, LDPE, polypropylene, acetal, Delrin, nylon, Pebax, other thermoplastic rubber, aliphatic or aromatic polyurethane, or a variety of other engineering resins that are well known to those skilled in the art. In embodiments, the inner shaft can be fabricated using multiple layers of two or three of the above-mentioned polymers to combine desirable properties of each.

For example, the outer surface could be composed of polyurethane to enable easier bonding of auxiliary components to the inner shaft. The inner layer could be PTFE to convey better lubricity to the inner shaft. In embodiments, the inner shaft and or the outer shaft could be coated on the inner and or outer surface with a coating material that conveys specific properties to the shaft like antithrombogenicity or lubricity. There are numerous available coating materials suitable for these purposes as are well known to those skilled in the art. The inner shaft can be compounded with a radiopacifier to increase the visibility of the inner shaft under fluoroscopy using bismuth salts such as bismuth subcarbonate, bismuth oxychloride, bismuth trioxide, tungsten powder, molybdenum powder or other radiopacifier such as are well known to those skilled in the arts. Similarly, the outer sheath can be fabricated from the same set of materials as the inner sheath, in the same manner and using the same coatings. Embodiments described below in connection with a flange rather than circumferential groove operate in substantially the same manner as described above and herein, except the device does not necessarily have projections that fit into and are retained by the grooves.

Figure 17:
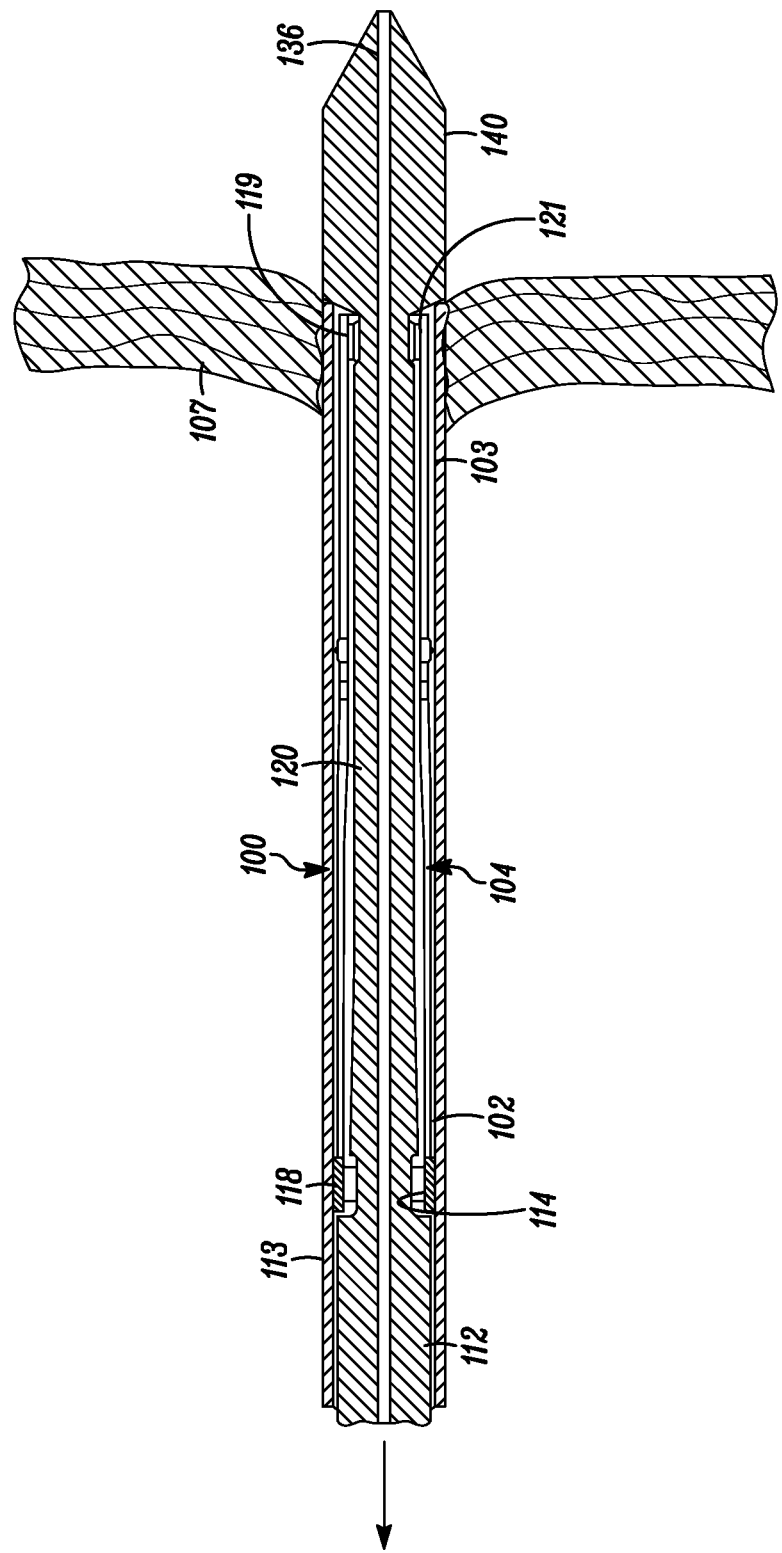
FIG. 17 is an enlarged cross-sectional detail view of the distal end of the placement catheter of FIG. 16 but showing the distal flange segments of the interatrial pressure vent being retracted from the interatrial septum as if it were determined to be in an undesirable position by imaging the radiopaque markers and going to be redeployed.

Referring now to FIG. 10, a folded representative interatrial pressure vent 100 of the present invention is shown in its stowed position with the placement catheter 111 of the present invention shown in its open position. In practice, if the body of the interatrial pressure vent is fabricated of nitinol or other elastic material, when the placement catheter is in its fully open position, the flange segments 102a-102h and 103a-103h would automatically recover into a shape like that shown in, for example, FIG. 4, hence this Figure is shown to illustrate the position of the interatrial pressure vent 100 relative to the waist section 120 and grooves 114 and 121. When radiopaque markers (or similarly dimensioned members) 118 extend beyond the thickness of the inside of body segment 101 of interatrial pressure vent 100, they form a projection within interatrial pressure vent 100 that can be captured within groove 114 to secure the position of the interatrial pressure vent 100 during placement. During deployment, the outer shaft 113 of placement catheter 111 is refracted a sufficient distance to reveal the distal portion of the interatrial pressure vent 100 allowing the flange segments 103a-103h to dilate radially away from the central longitudinal axis of body 101. By capturing the radiopaque 118 markers within the groove 114, the device can be repositioned easily without further deployment, or the device can be completely retracted and removed from the patient without deployment as indicated in FIG. 17.

Referring now to FIG. 11, an interatrial pressure vent 100 of the present invention is shown completely stowed within the placement catheter 111 of the present invention.

Figure 11A:
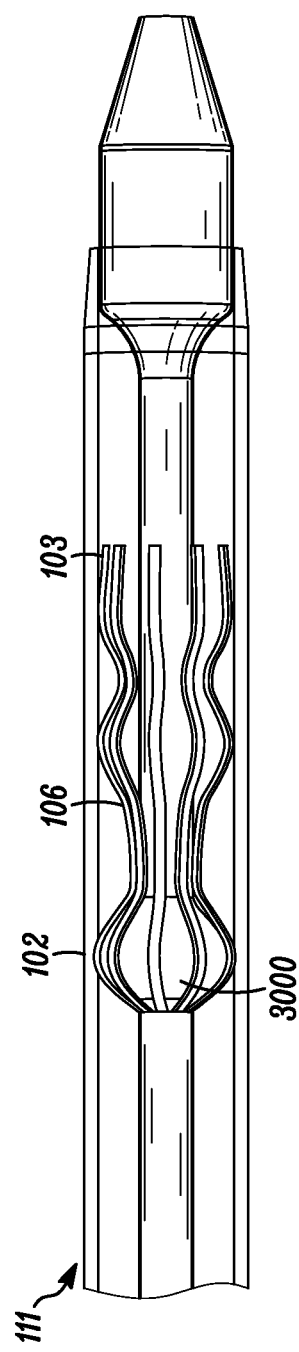
FIG. 11A is a side view of another embodiment of a placement catheter with an interatrial pressure vent stowed therein.

FIG. 11A shows an embodiment of the placement catheter similar in operation to those described herein but operative to engage an interatrial pressure vent by way of a slightly different mechanism than described above in connection with circumferential grooves. This figure shows a schematic depiction of a stowed interatrial vent. Rather than having the grooves as described above, this embodiment of a placement catheter comprises an inner shaft having a flange or member 3000 (rather than a groove) which has a diameter larger than that of the inner shaft to grip and hold an end of the interatrial vent device as shown. As shown in the figure, the flange and its segments (collectively referred to in the figure as 102) wrap around the ball-shaped flange 3000 and allow the interatrial pressure vent to be moved with the placement device in the manners described herein.

Figure 12:
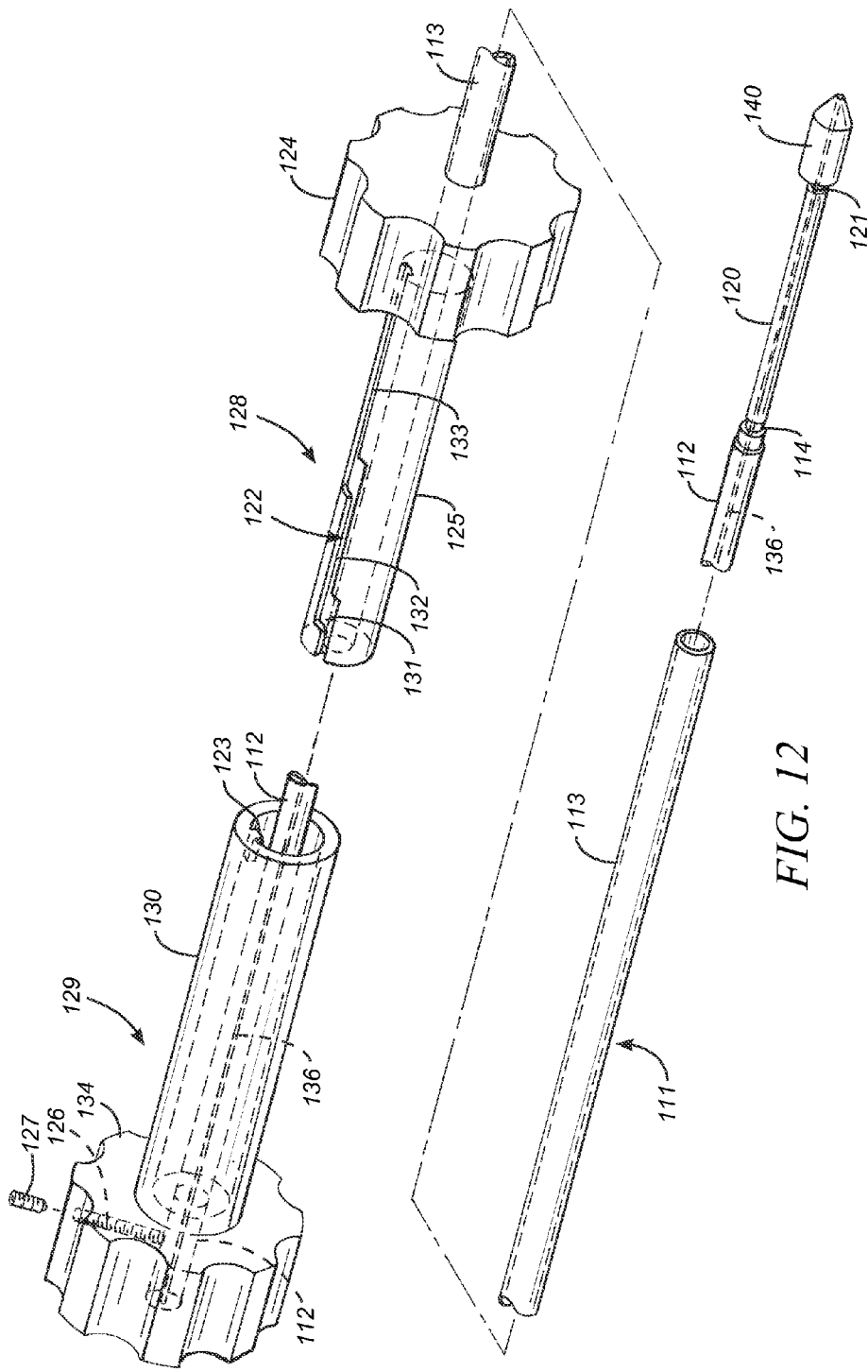
FIG. 12 is an exploded perspective view of the proximal and distal ends of a placement catheter.

Referring now to FIG. 12, a placement catheter 111 of the current invention is shown. It should be noted that while the inner shaft is depicted as having grooves in FIG. 12, the inner shaft may comprise the flange 3000 as described above in connection with FIG. 11A. The skilled artisan will appreciate that the operation of the device is substantially similar whether grooves or flanges are utilized. The placement catheter 111 comprises a first handle component 128 that can be attached to outer shaft 113. The first handle component can be attached to the outer shaft 113 using a variety of adhesive methods such as solvent bonding using a solvent for both the handle and outer shaft material; an organosol consisting of a solvent and polymer in solution that is compatible with both the outer shaft and the first handle component; a polymerizable adhesive, such as polyurethane, cyanocrylate, epoxy or a variety of other adhesives as are well known to those skilled in the art. The first handle component can be fabricated from a variety of metals such as aluminum, stainless steel, titanium or a number of other metals and alloys as are well known to those skilled in the art. In embodiments, the first handle component 128 is fabricated from a polymer such as polycarbonate, or a variety of engineering resins, such as Lexan, or others as are well known to those skilled in the art. The first handle component comprises hand grip section 124 and tubular shaft section 125. The tubular shaft section 125 can contain keyway 122 that is formed or machined into the shaft section. The keyway is preferably formed with three linear sections; a first linear section 131, a second linear section 132 and a third linear section 133. Each of these sections is formed to traverse along a path primarily parallel with the center axis along the length of the first handle component but each is displaced radially from one another by at least about half of the width of the keyway. The placement catheter 111 also can comprise a second handle component 129 that can be attached to inner sheath 112. The second handle component can be fabricated from the same variety of metals and polymers as the first handle component. The two handles can be fabricated from the same materials or from different materials. The second handle component can be attached to the inner sheath in the same manner and using the same materials as the first handle component attaches to the outer sheath. In embodiments, the second handle component can contain threaded hole 126 for containing set screw 127. The set screw can be twisted to capture the inner shaft against the second handle component. The second handle component 129 also can comprise a second hand grip section 134 and second tubular shaft section 130. The second tubular shaft section can contain key 123 that is formed or machined of suitable dimension to adapt to keyway 122 of first handle component 128. When assembled, second handle component 129 can be slideably moved relative to first handle component 128 in a manner controlled by the shape and length of the key way 122. As the second handle 129 is advanced relative to the first handle 128, it can be appreciated that the inner sheath 112 will slide in a distal direction out from the outer sheath 113. It can be appreciated that when the second handle component 129 is assembled, the key 123 is slid into the first linear section 131 and advanced until it hits the edge of the keyway formed between the first linear section 131 and the second linear section 132. In order for the second handle component 129 to advance further, it must be rotated and, once rotated, it can be advanced further but will stop when the key 123 hits the edge of the keyway formed between the second linear section 132 and the third linear section 133. The keyway dimensions are preferably selected with consideration for the combination of lengths of other components in the placement device. A first position, defined as the position when the key 123 is in contact with the proximal edge formed between the first linear section 131 and the second linear section 132, is preferably determined so, when fully assembled and with the interatrial vent in its stowed position within the placement catheter, the outer shaft 113 will completely cover the length of the interatrial pressure vent 100 as is desired during catheter placement. The keyway dimensions can also be selected to result in a second position, defined as the position when the key 123 is in contact with the distal edge formed between the second linear section 132 and third linear section 133. The second position would preferably be selected to reveal the full length of flange segments 103a-103h but retain flange segments 102a-102h within the outer shaft 113 of the catheter. The length of the third linear section 133 would preferably be selected so that, when the second handle component 129 was advanced completely against the first handle component 128, the full length of the interatrial vent 100 would be uncovered by the outer shaft 113 and the device would be deployed. A variety of other configurations of the first and second handle components could be used for this same purpose. The first handle component tubular shaft section 125 and the second handle component tubular shaft section 130 could be threaded (not shown) so the first handle component 128 could be screwed into the second handle component 129. Alternatively, gear teeth (not shown) could be formed in the first tubular shaft section 125 of the first handle component 128 and a gear wheel (not shown) could be incorporated into the second shaft tubular section 130 of the second handle component 129. The gear wheel would preferably be chosen to mesh with the gear teeth and the second handle component 129 could be advanced toward the first handle component 128 by rotating the gear wheel. A variety of other design configurations could be utilized to control the relative location between the first handle component and the second handle component as are well known to those skilled in the art.

FIGS. 13 through 17 show embodiments of a system for treating heart failure of the present invention. More specifically FIGS. 12 through 19 show how the placement catheter is introduced and positioned in a patient and methods for placing the interatrial valve in a patient. The interatrial pressure vent 100 is presterilized and packaged separately from the placement catheter 111. Sterilization can be performed by exposing the device to a sterilizing gas, such as ethylene oxide, by exposing the device to elevated temperature for an adequate period of time, by using ionizing radiation, such as gamma rays or electron beam or by immersing the device in a fluid that chemically crosslinks organic molecules, such as formaldehyde or gluteraldehyde and then rinsed in sterile water or sterile saline. For each of these sterilization methods, consideration must be given to compatibility of the materials so device performance is not adversely affected as a result of the sterilization process. Also, the packaging design and materials must be carefully considered with the sterilization procedure, post sterilization handling and storage, environmental exposure during storage and shipment, and ease of handling, opening, presentation and use during the procedure.

In embodiments, interatrial pressure vent 100 can be assembled using components that have been pre-sterilized using one of the above methods or others that are well known and the final assembly may be accomplished in an aseptic manner to avoid contamination.

In embodiments, the interatrial pressure vent 100 can be supplied non-sterile and be sterilized around the time of use using one of the above methods or by other methods well known by those skilled in the art.

Similarly, the placement catheter 111 may be pre-sterilized and packaged separately from the interatrial pressure vent 100. Sterilization can be performed using a similar method to the interatrial pressure vent 100 or using a different method from the same choices or using some other method as is well known by those skilled in the art.

In embodiments, an interatrial pressure vent 100 and the placement catheter 111 can be supplied pre-sterile and in the same package. In another aspect, the interatrial pressure vent 100 and the placement catheter 111 can be preloaded and supplied pre-sterile.

Prior to insertion, the interatrial pressure vent 100 is preferably folded and stowed onto the placement catheter 111. This can be accomplished in a sterile field and using aseptic techniques in the following steps. First the interatrial pressure vent 100 is presented to the sterile field and the placement catheter 111 is presented to the sterile field. Second, the interatrial pressure vent 100 and placement catheter 111 are inspected for visible signs of damage, deterioration or contamination. Third, the second handle component 129 of the placement catheter 111 is retracted fully so the outer shaft 113 exposes the inner shaft 112 to the maximum extent allowed. Fourth, the interatrial pressure vent 100 is positioned in the correct orientation over the inner shaft 113 of the placement catheter 111 with the inner shaft 113 oriented through the center of the flow control element 104. Fifth, the flange segments 102a-h and 103a-h are folded away from each other and the flange segments 102a-h and 103a-h and the core segment 106 are compressed radially to fold the interatrial pressure vent 100 into a size and shape that will fit over and onto the waist section 120 of the inner shaft 112 with the distal ends 115 of flange segments 102a-h aligning with the proximal groove 114 of inner shaft 112. In embodiments comprising a flange as described in FIG. 11A the flange segments 102a-h and 103a-h are folded away from each other and the flange segments 102a-h and 103a-h and the core segment 106 are compressed radially to fold the interatrial pressure vent 100 into a size and shape that will fit over the flange 3000 described on FIG. 11A. This folding may be accomplished with the aid of an insertion tool (not shown) that retains the interatrial pressure vent 100 in a stowed position on inner shaft 112 and then advancing outer shaft 113 over the stowed interatrial pressure vent 100 and displacing the insertion tool, thereby leaving the outer shaft 113 completely covering the interatrial pressure vent 100 and mating with the distal tapered tip 140 of the inner shaft 112. In other embodiments, this can be accomplished by hand using the fingers of one hand to hold the distal ends 115 of the flange segments 102a-102h in position at groove 114 of the inner shaft 112 and advancing the outer shaft 113 over the inner shaft 112 enough to hold the flange segments 102a-102h in place. Completion of the loading procedure is accomplished by progressively advancing the outer shaft 113 until it completely covers the interatrial pressure vent 100 as shown in FIGS. 11 and 11A. While the below discussion regarding placement of the interatrial pressure vent uses the placement device shown in FIGS. 9-11 as an example, the description on placement and the procedure therefore is also meant to apply to embodiments where the inner shaft comprises a flange rather than grooves.

Figure 13:
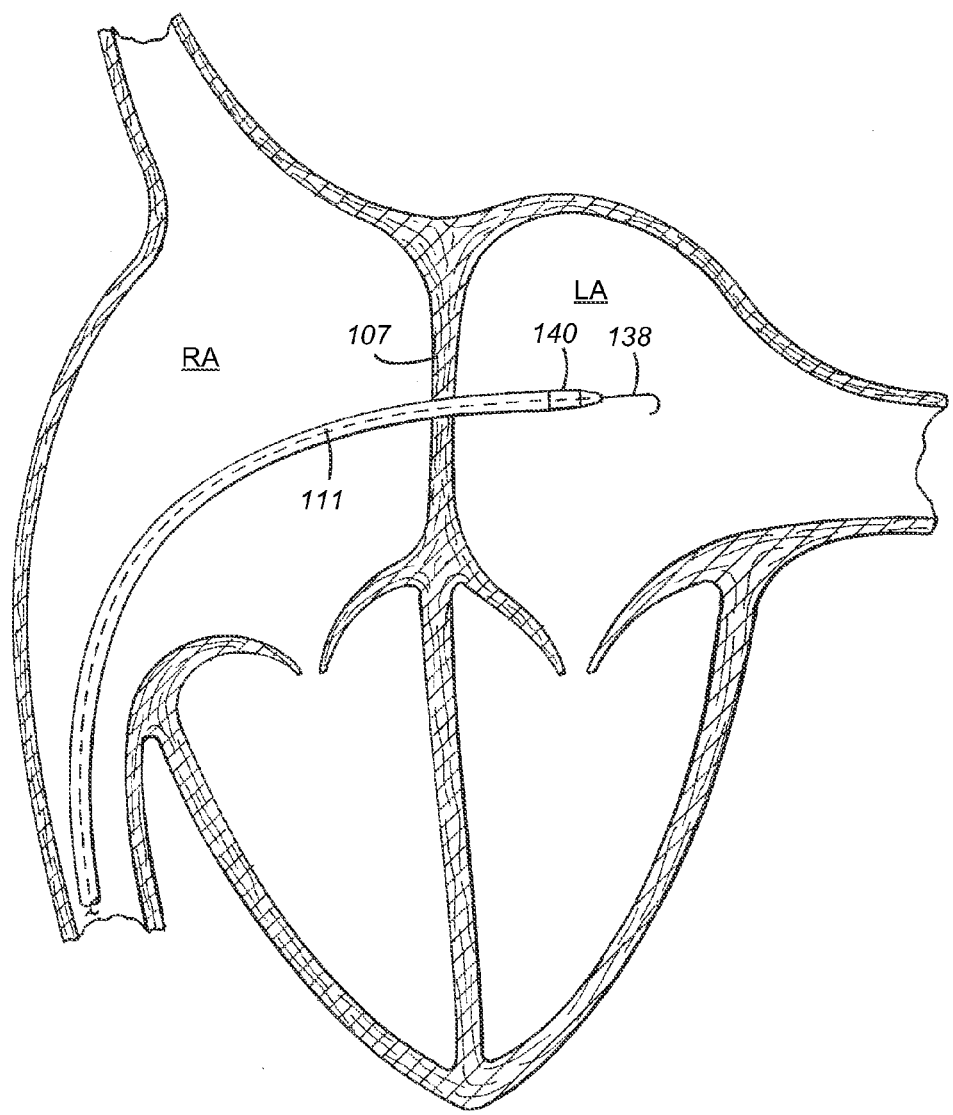
FIG. 13 is a cutaway view of a heart of a patient and the distal end of a placement catheter in position across the interatrial septum.

Positioning of the loaded interatrial valve 100 and placement catheter 111 in preparation for implanting the interatrial valve 100 in the patient can be accomplished by: first gaining vascular access; second, positioning a guidewire 121 in the right atrium of the patient; third, positioning an introducer (not shown) into the patients right atrium; fourth, locating the interatrial septum; fifth, advancing the introducer through the interatrial septum and into the patient's left atrium; sixth, advancing the guidewire 138 into the left atrium; seventh, retracting the introducer; eighth, advancing the loaded placement catheter 111 and interatrial pressure vent 100 into position so the distal end and approximately half of the stowed length of the interatrial pressure vent 100 is protruding through the interatrial septum and into the patient's left atrium as shown in FIG. 13.

In embodiments, positioning of the loaded interatrial valve 100 and placement catheter 111 in preparation for implanting the interatrial valve 100 in the patient can be accomplished by: first gaining vascular access; second, positioning a guidewire 138 in the right atrium of the patient; third, advancing the loaded interatrial valve 100 and placement catheter 111 over guidewire 138 by inserting the guidewire into and through lumen 136 and advancing placement catheter 111 into the patient's right atrium; fourth, locating the interatrial septum; fifth, advancing the placement catheter 111 through the interatrial septum and into the patient's left atrium so the distal end and approximately half of the stowed length of the interatrial pressure vent 100 is protruding through the interatrial septum and into the patient's left atrium as shown in FIG. 13.

Figure 14:
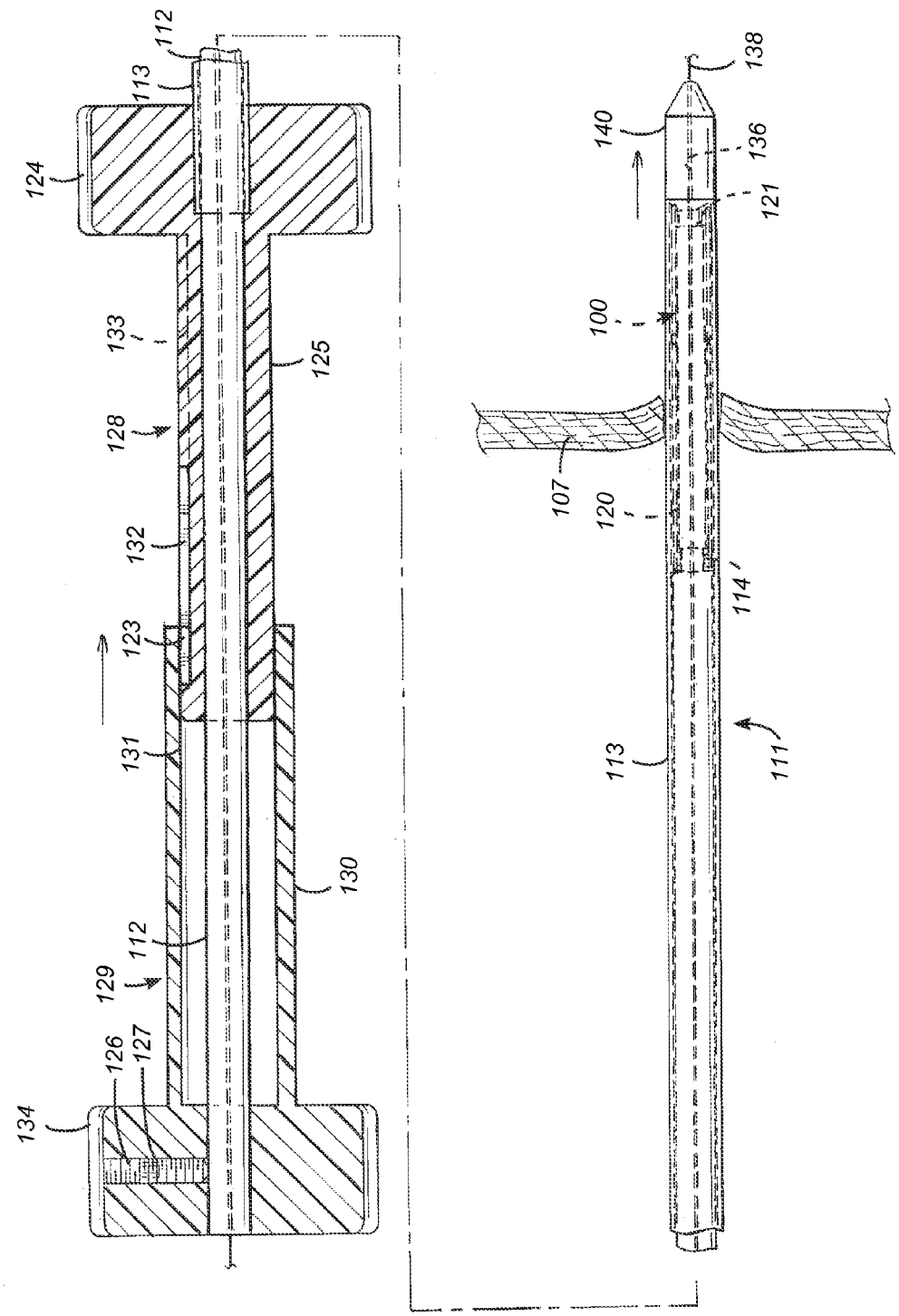
FIG. 14 is a schematic cross sectional side view of the proximal and distal end of a placement catheter in a closed position and positioned across the interatrial septum of the heart of a patient.
Figure 15:
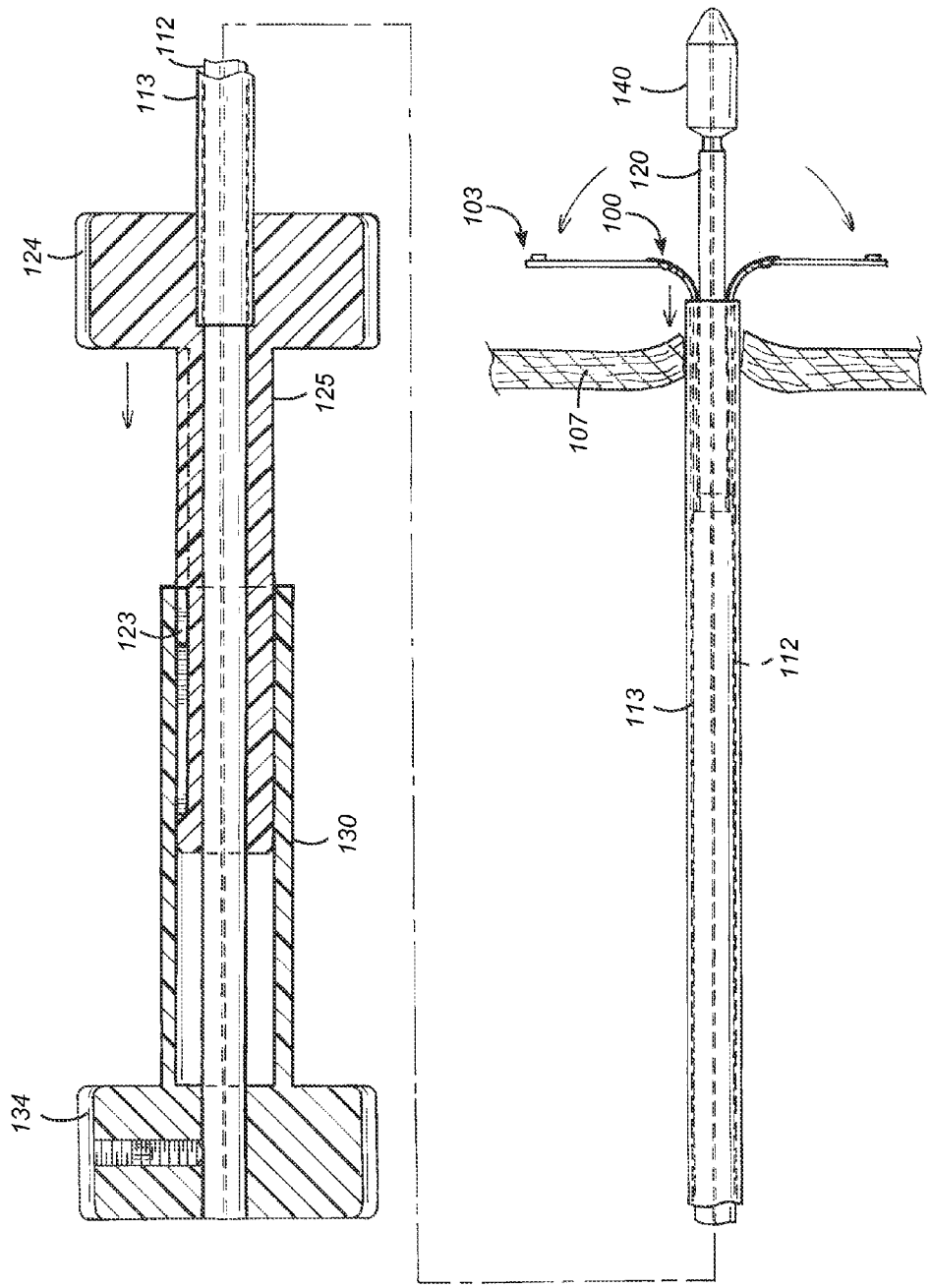
FIG. 15 is a view similar to FIG. 14 but showing the distal end of the placement catheter in a partially open position and the distal flange segments of the interatrial pressure vent deployed.
Figure 16:
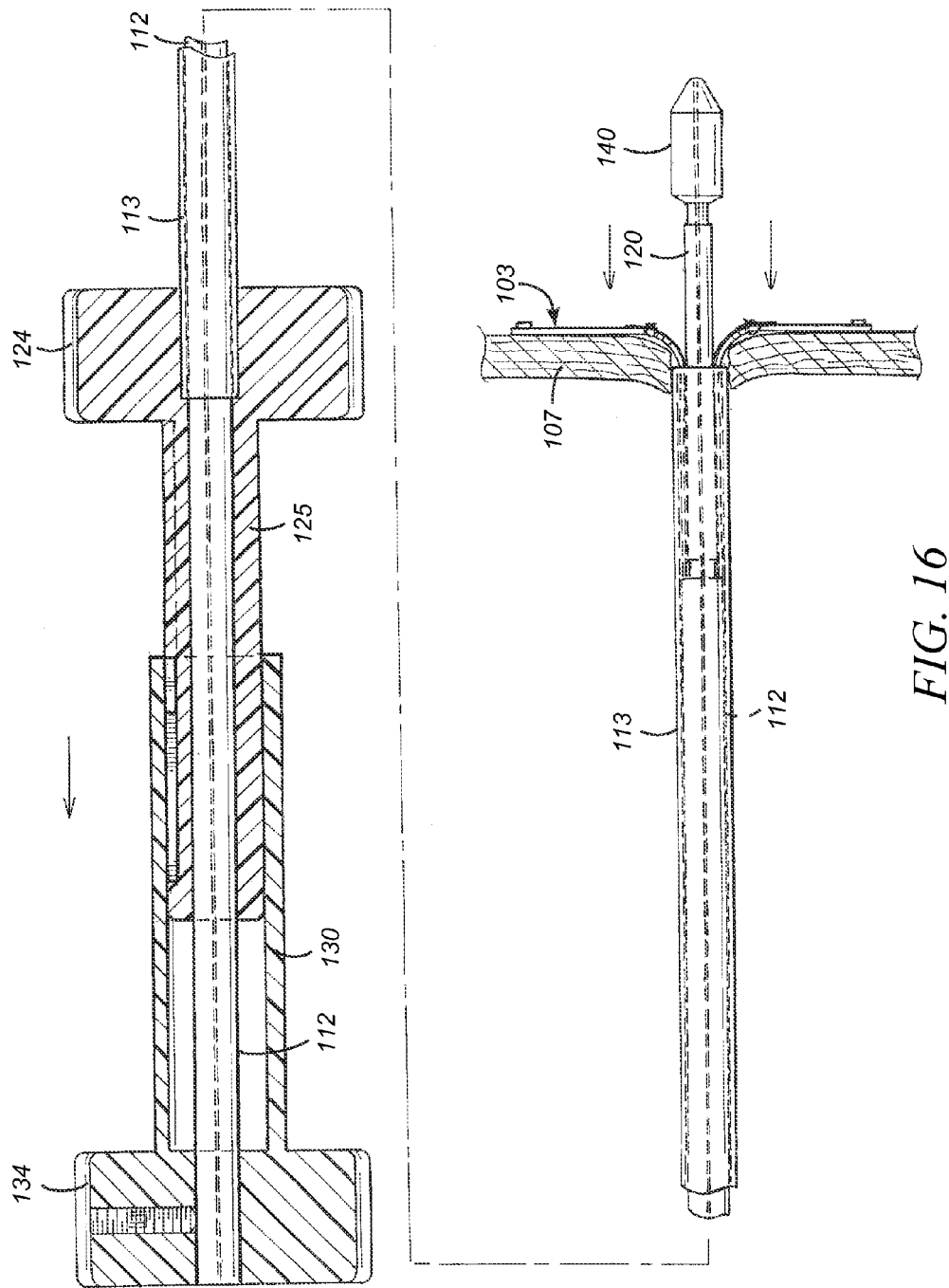
FIG. 16 is a view similar to FIG. 15 but showing the distal flange segments of the interatrial pressure vent in position against the wall of the interatrial septum.
Figure 18:
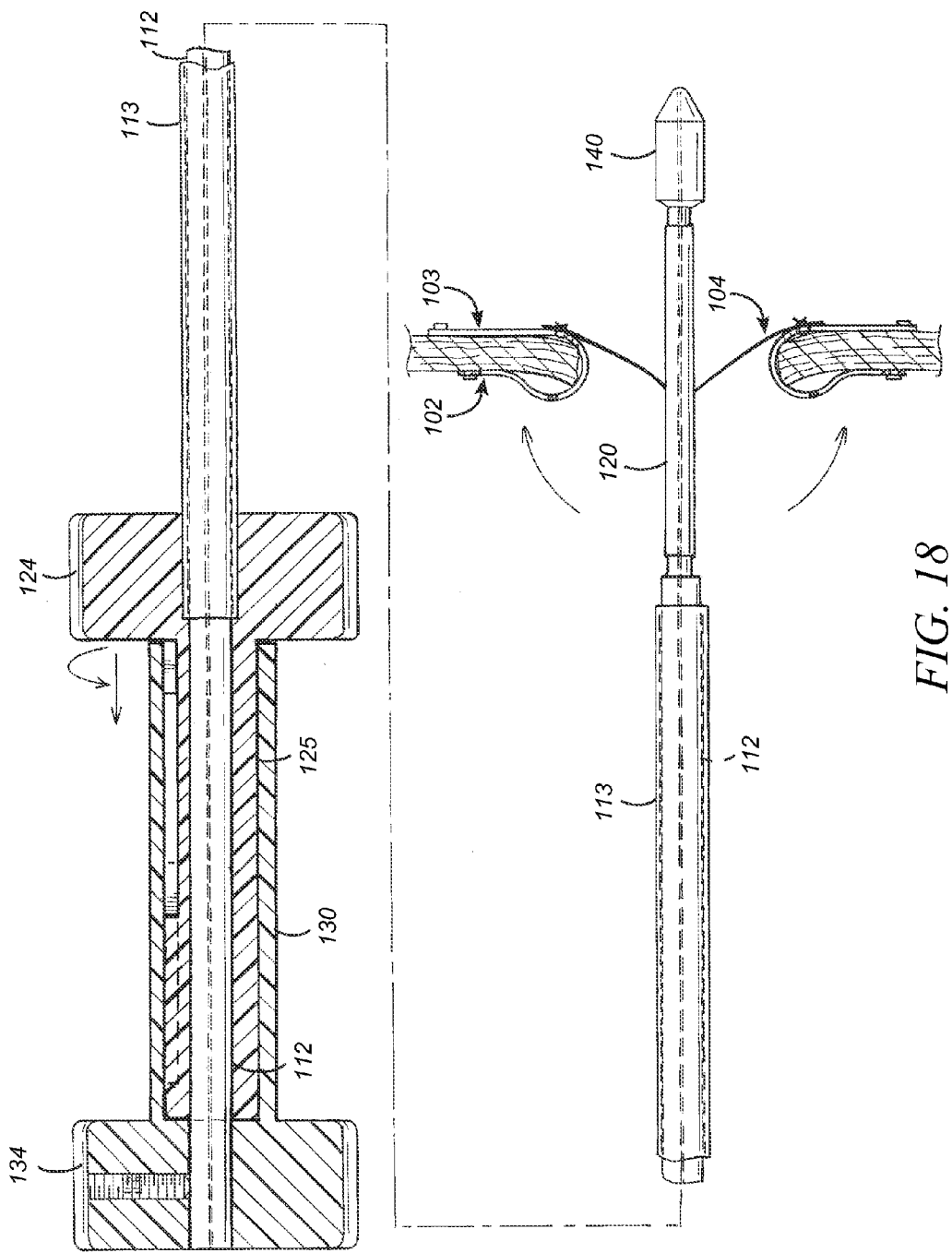
FIG. 18 is a view similar to FIG. 16 but showing further deployment of the interatrial pressure vent by releasing the proximal flange segments if imaging determines a correct positioning of the distal flange segments.
Figure 19:
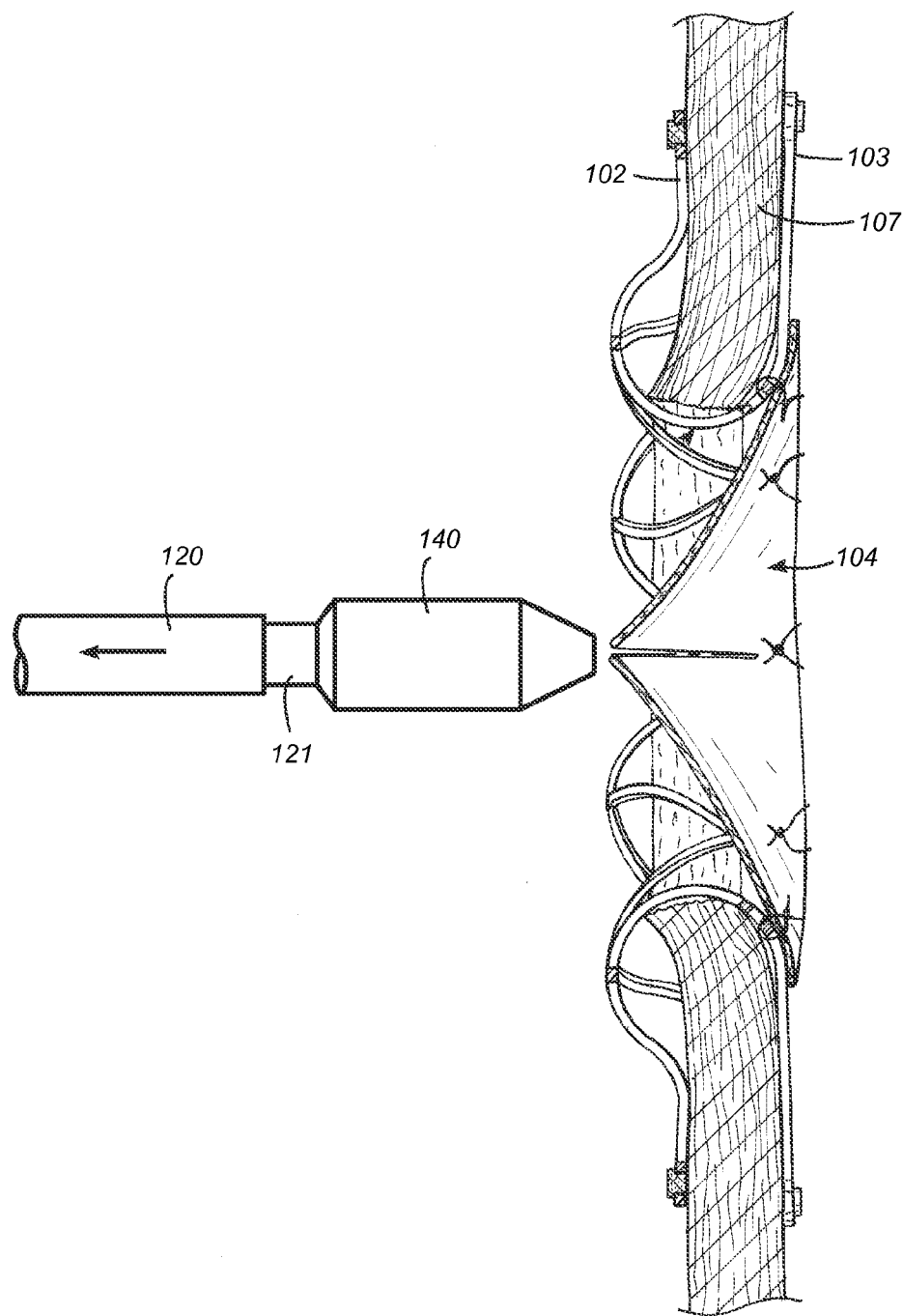
FIG. 19 is an enlarged cross-sectional detail view of the placement; catheter of FIG. 18 but showing the interatrial pressure vent fully released in position and the placement catheter being removed.

Implanting interatrial pressure vent 100 into a patient can be accomplished, once the loaded interatrial pressure vent 100 and placement catheter 111 are in position as shown in FIG. 14, by first, retracting first handle component 128 toward second handle component 129 while holding second handle component 129 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by retracting first handle 128 toward second handle 129 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fourth, the inner sheath is retracted through the flow control element 104 of interatrial pressure vent 100, into the patient's right atrium as shown in FIG. 19; fifth, the first handle component 128 is advanced away from the second handle component 129 to reposition inner shaft 112 into the position relative to outer shaft 113 it was in during placement and the placement catheter is removed from the patient and the procedure is completed.

In other embodiments, implanting interatrial pressure vent 100 into a patient can be accomplished, once the loaded interatrial pressure vent 100 and placement catheter 111 are in position as shown in FIG. 14, by first, advancing second handle component 129 toward first handle component 128 while holding first handle component 128 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by advancing second handle 129 toward first handle 128 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fourth, the inner sheath is retracted through the flow control element 104 of interatrial pressure vent 100, into the patients right atrium as shown in FIG. 19; fifth, the second handle component 129 is retracted away from the first handle component 128 to reposition inner shaft 112 into the position relative to outer shaft 113 it was in during placement and the placement catheter is removed from the patient and the procedure is completed.

For a variety of reasons, it may be necessary or desirable to remove interatrial pressure vent 100 and placement catheter 111 during any part of the procedure without further risk or injury to the patient. This is possible as follows: if, for any reason, it is desired for the device to be removed before outer shaft 113 is retracted and flange segments 103a-h are deployed, then the placement catheter 111 with interatrial valve 100 can simply be retracted out through the same pathway as introduced.

If, following deployment of flange segments 103a-h it is necessary or desirable to remove the device, then the interatrial valve 100 can be retracted into the placement catheter 111 by advancing first handle 128 away from second handle 129, while holding second handle 129 stationary, thereby advancing outer sheath 113 distally through the interatrial septum and over the flange segments 103a-h. In embodiments, radiopaque markers 118 placed in marker holes 109 are captured in groove 114 (see FIG. 17) and cannot fit in the gap between waist 120 of inner shaft 112 and inner surface of outer shaft 113, so as outer sheath 113 is advanced, flange segments 103a-h are forced to fold inward toward their stowed position and are retracted back onto inner shaft 112 and within outer sheath 113. Once outer shaft 113 is fully advanced, catheter 111 can be retracted as shown in FIG. 17 to be removed out through the interatrial septum and out through the same pathway as introduced.

Figure 19A:
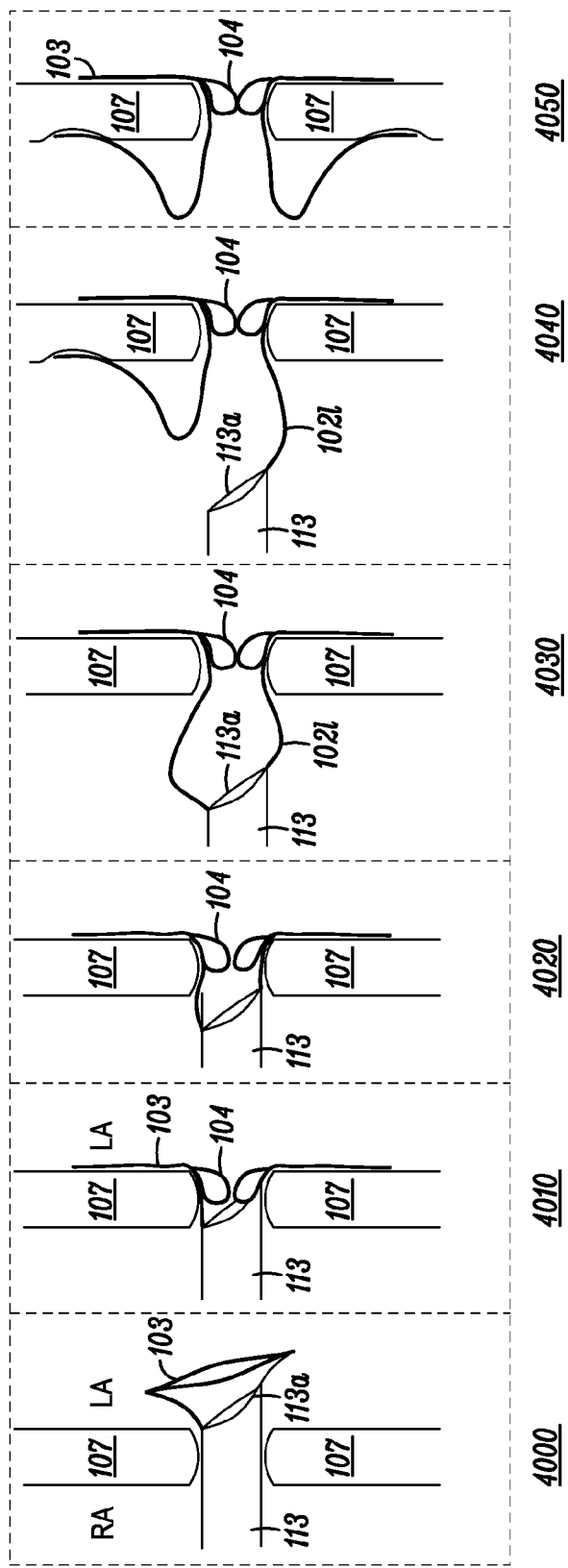
FIG. 19A is schematic depiction of another embodiment of a placement catheter system and interatrial pressure device along with the deployment process therefor.

FIG. 19A is embodiment of the invention designed to enhance the retrievability of the device. The procedure for implanting the device is substantially similar to that which is described above; however, there are variations to the placement catheter and the device, which will be described below. As discussed in connection with FIGS. 7A through 7C, embodiments of the interatrial venting device comprise at least one flange segment being longer than the other flange segments. The embodiment schematically shown in FIG. 19A preferably works with such embodiments having at least one flange segment that are longer in relation to the other flange segments; thus the segments shown in the RA have the same reference number as the longer segments in FIGS. 7A through 7C, i.e., 102L. In embodiments utilizing the techniques shown in FIG. 19A, the opening 113a of outer sheath 113 of placement catheter is angled or has a more surface area on one side relative to the other. The placement catheter is oriented during the procedure such that the angled opening (or the plane of the opening itself) is at an angle more normal to the septal wall 107. In the embodiment shown in FIG. 19A, that angle appears to be around 45 degrees with respect to the septal wall 107, but any angle which provides an more normal angle with respect to the septal wall may be used, and any opening which provides more surface area of the outer sheath 113 on one side with respect to the other side may be used. Reference numerals 4000 through 4050 refer to steps in the process described below. The process is largely similar to that described above or with respect to any well-known placement catheter system and process, therefore only the applicable differences will be described. As can be seen at steps 4000 through 4020, the placement catheter is positioned and the device is in the beginning stages of deployment. At steps 4030 and 4040, the as the outer sheath 113 is retracted and on the RA side (or when the inner shaft is advanced while the outer sheath is on the RA side, which is not shown), the opening allows one of the longer flange segments 102L to be deployed after other flange segments have been deployed and are thus in contact with the septum 107. The at least one longer flange segment 102L is retained in the placement catheter system by way of the outer sheath 113, the length of which extends further on one side than the other due to the opening and thus covers the longer segment 102L while the other shorter segments have been deployed. In this way, the operator of the placement catheter can determine if the interatrial device is in the proper position. If not, the operator can still retrieve the device up until the last point prior to full deployment, i.e., when at least one of the longer flange segments (102L for example) is still retained in the placement catheter by the outer sheath 113. If it is in proper position, the deployment may commence.

Figure 19B:
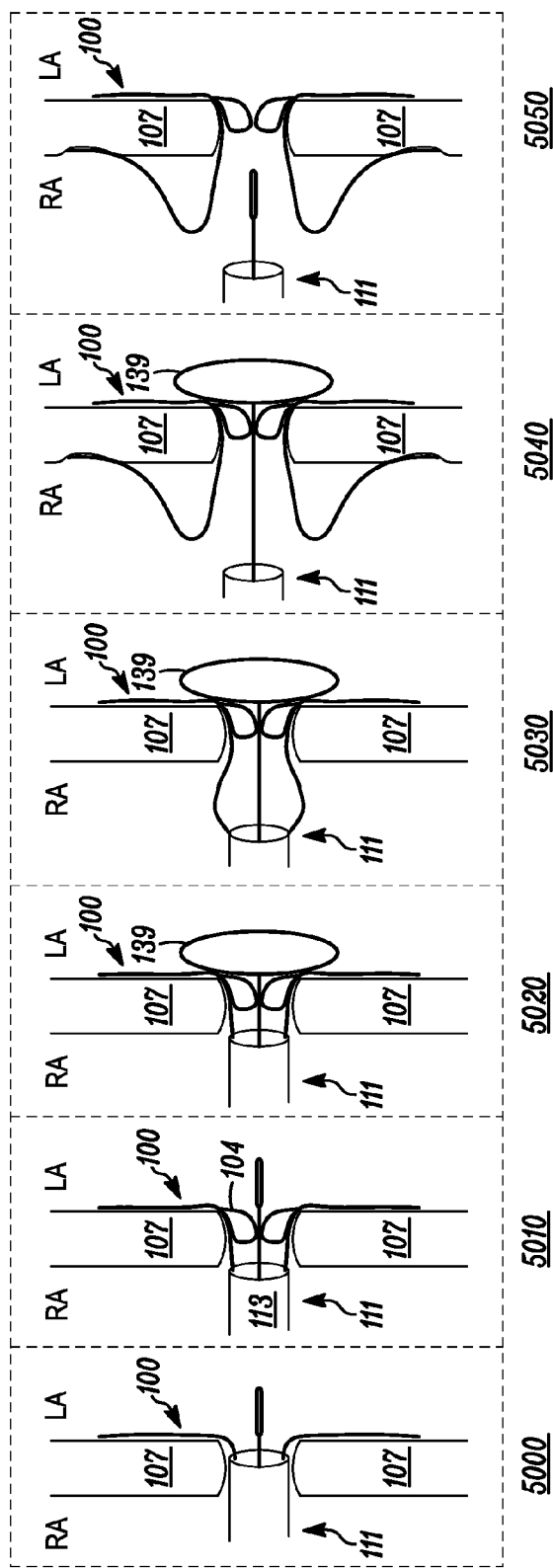
FIG. 19B is schematic depiction of another embodiment of a placement catheter system and deployment process therefor.

Another deployment embodiment is now described in connection with FIG. 19B. This deployment embodiment may be used with any embodiment of the interatrial vent described herein. Reference numerals 5000 through 5050 refer to steps in the process described below. At step 5000, the LA side of the device (generally referred to in this figure as 100) is deployed on the LA side of the heart. Further deployment is shown at step 5010 and the outer sheath is retracted into the RA side of the heart, which allows flow control element 104 to exit the placement catheter. Placement catheter is equipped with a balloon, which is in fluid communication, for example, with lumen 136 described above or guide wire 138. The skilled artisan will appreciate other configurations in which a balloon catheter may be provided in the placement catheter system. Upon deployment of the LA side flange or shortly thereafter, balloon 139 is inflated (shown in step 5020). The inflation of the balloon optionally coupled with a pulling-back motion of the placement catheter 111 holds the device 100 against the LA side of the septal wall 107 and thereby prevents the device 100 from dislodging during deployment and/or moving in a direction away from the septal wall. Step 5040 shows the full deployment of the device 100 while the balloon 139 is inflated. When satisfactory deployment is achieved, the balloon 139 is deflated and the placement catheter system is removed (shown at step 5050).

Figure 20:
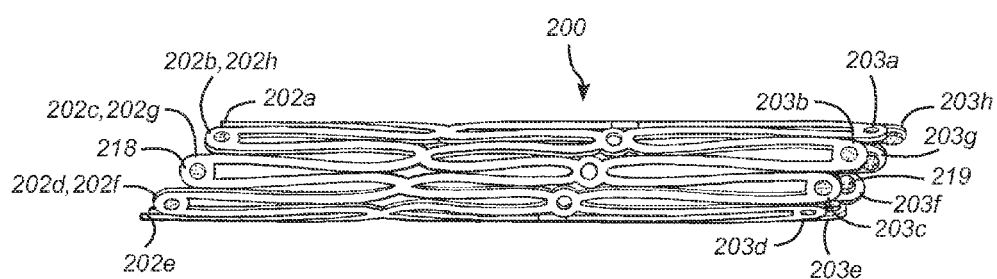
FIG. 20 is a side elevational view of an alternate embodiment of an interatrial pressure vent body with slanted flange segment ends.

Now referring to FIG. 20, an interatrial pressure vent 200 of the present invention is shown. In embodiments, flange segments 202a-h and 203a-h can be formed with graduating length to reduce interference between flange segments 202a-h and 203a-h during handling, folding and loading. In embodiments, radiopaque markers 218 and 219 protrude into the inner cylindrical shape of the stowed position of the interatrial pressure vent and each flange segment 202a-h and 203a-h differs in length by at least the width of the radiopaque markers 218 and 219. In embodiments, each flange segment 202a-h and 203a-h differs in length by at least at least 1 mm. In embodiments, each flange segment 202a-h and 203a-h differs in length by at least 2% of the overall length of interatrial pressure vent 200 in the position shown in FIG. 20.

Figure 21:
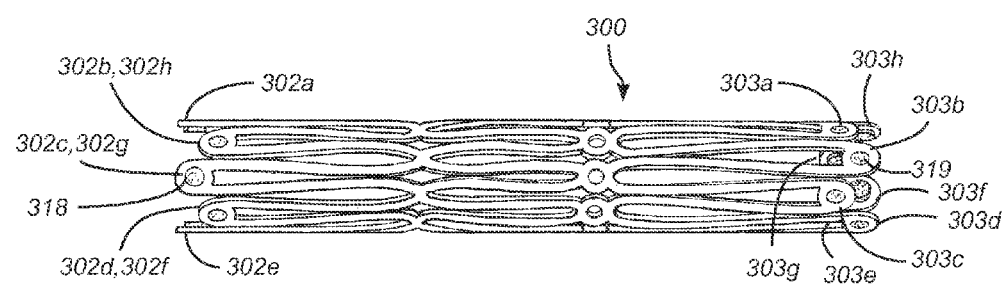
FIG. 21 is a side elevational view of an alternate embodiment of an interatrial pressure vent body with staggered flange segment ends.

Now referring to FIG. 21, an interatrial pressure vent 300 of the present invention is shown. In embodiments, flange segments 302*a-h* and 303*a-h* can be formed with alternating length to reduce interference between flange segments 202*a-h* and 203*a-h* during handling, folding and loading. In embodiments radiopaque markers 318 and 319 protrude into the inner cylindrical shape of the stowed position of the interatrial pressure vent 300 and alternating flange segments 302*a, c, e,* and *g* are longer than flange segments 302*b, d, f* and *h,* and correspondingly, flange segments 303*b, d, f* and *h* are longer than flange segments 303*a, c, e* and *g* by at least the width of the radiopaque marker. In embodiments, alternating flange segments 302*a, c, e* and *g* are longer than flange segments 302*b, d, f* and *h* and, correspondingly, flange segments 303*b, d, f* and *h* are longer than flange segments 303*a, c, e* and *g* by at least 1 mm. In one aspect the alternating flange segments 302*a, c, e* and *g* are longer than flange segments 302*b, d, f* and *h* and, correspondingly, flange segments 303*b, d, f* and *g* are longer than flange segments 303*a, c, e* and *g* by at least 2% of the overall length of interatrial pressure vent 300 in the position shown in FIG. 21.

Figure 22:
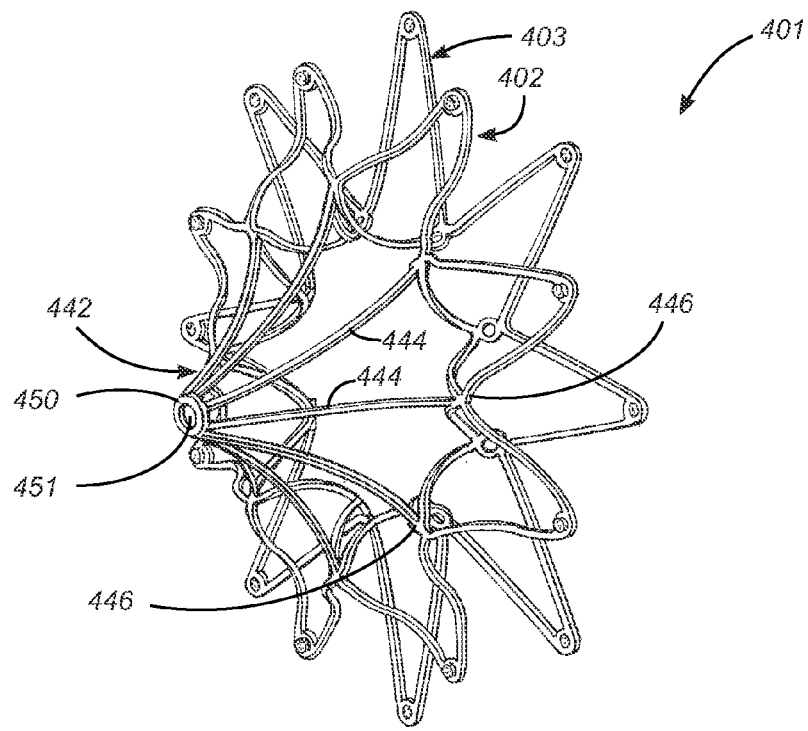
FIG. 22 is a perspective view of an alternate embodiment of an interatrial pressure vent body with an integrated retrieval means and thrombus clot strainer.
Figure 23:
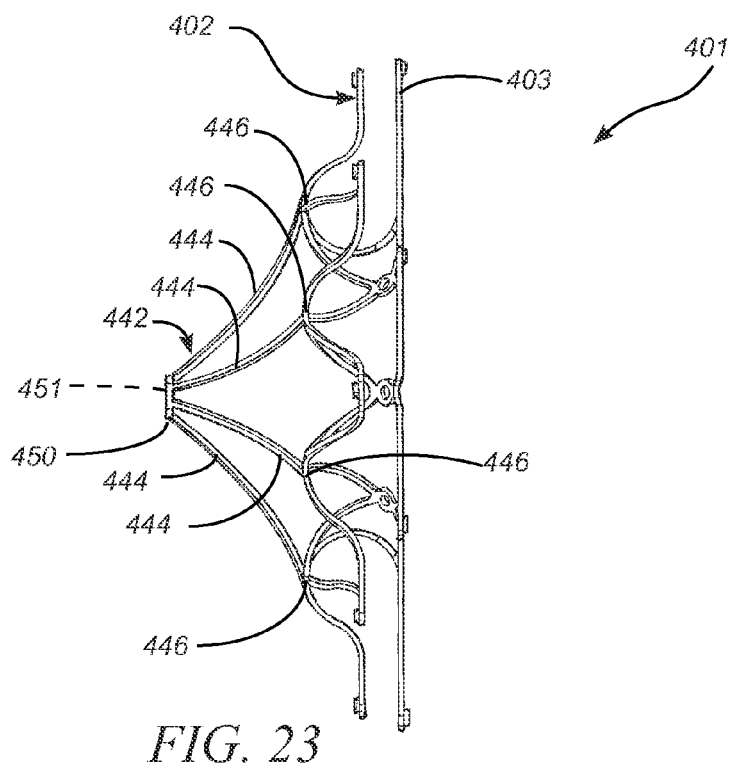
FIG. 23 is a right side view of the body assembly of FIG. 22.

Referring now to FIG. 22 and FIG. 23, the body element 401 of an interatrial pressure vent with integral thrombus filter and retrieval cone 442 of the present invention is shown. In embodiments, conical struts 444 are affixed to body element 401 at attachment points 446 and converge at apex 450. In embodiments, conical struts 444 comprise single beams of similar material to flange segments 402 and 403 and can be attached to the body element or formed at the same time as the body element using techniques described in this specification, and are thus integral with the remainder of the device. In embodiments the space between adjacent struts 444 is about 2 mm. In embodiments, the space between adjacent struts 444 is about 4 mm. As can be appreciated, conical struts 444 will protrude into the right atrium of the patient after implant and spaces between conical struts will function to block the passage of solid material larger than the space between adjacent struts 444. This will provide the function of preventing emboli that are larger than the space between the adjacent struts 444 from passing from the right atrium to the left atrium.

Referring again to FIG. 22 and FIG. 23, in embodiments the shape of the conical struts 444 is not straight. In embodiments the shape of the conical struts 444 can be concave when viewed on end as depicted in FIG. 22. In embodiments the conical struts can be curved in a direction away from the chord formed between the apex 450 and the attachment points 446. In embodiments there can be a hole 451 through apex 450 large enough to receive a retrieval snare (not shown). It can be appreciated that conical struts 444 and apex 450 can be used to aid retrieval of the interatrial pressure vent from a patient at some time after the implant procedure using a method as follows: A catheter tube with an internal lumen at least as large as apex 450 can be placed into the patients right atrium using standard techniques and imaging equipment. A retrieval snare can be fabricated from the proximal end of a guidewire bent sharply by about 180 degrees and this snare can be inserted through the catheter tube and advanced into the patient's right atrium and with the assistance of fluoroscopy advanced through hole 451 or around conical struts 444. Once the retrieval snare is engaged in this manner, it will be possible to retract the interatrial pressure vent by advancing a catheter tube while holding slight tension on the snare and thereby guide the catheter tube over apex 450 and onto conical struts 444. As the catheter tube continues to advance, with some tension on the snare it will be possible to force the conical struts inward, thereby forcing the flange segments 402 to begin folding inwards. When the conical struts are nearly completely in the catheter tube, the catheter tube can be held in a stationary position and the snare wire retracted against it, thereby causing the attachment points 446 between the conical struts 444 and the flange segment 402 to be retracted into the catheter. Flange segments 402 can begin to be retracted into the catheter at this point and the distal ends of flange segments 402 can be diverted toward the patients left atrium but will also fold inward and into the catheter. Once the flange segments 402 are inside of the catheter tube, the snare can be held stationary and the catheter tube can be advanced further, through the interatrial septum and over flange segments 403. Once the flange segments 403 are retracted into the catheter, the catheter and snare can be moved together to retract the interatrial pressure vent into the patient's right atrium and out through the pathway through which it was introduced.

Figure 24:
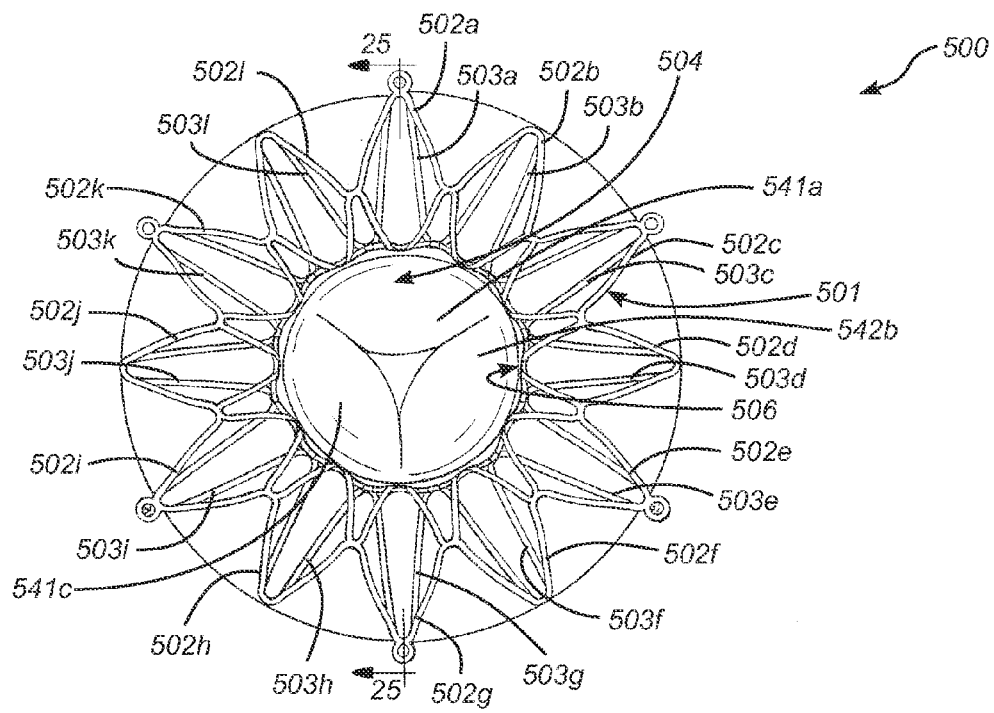
FIG. 24 is an end view of an alternate embodiment of interatrial pressure vent.
Figure 25:
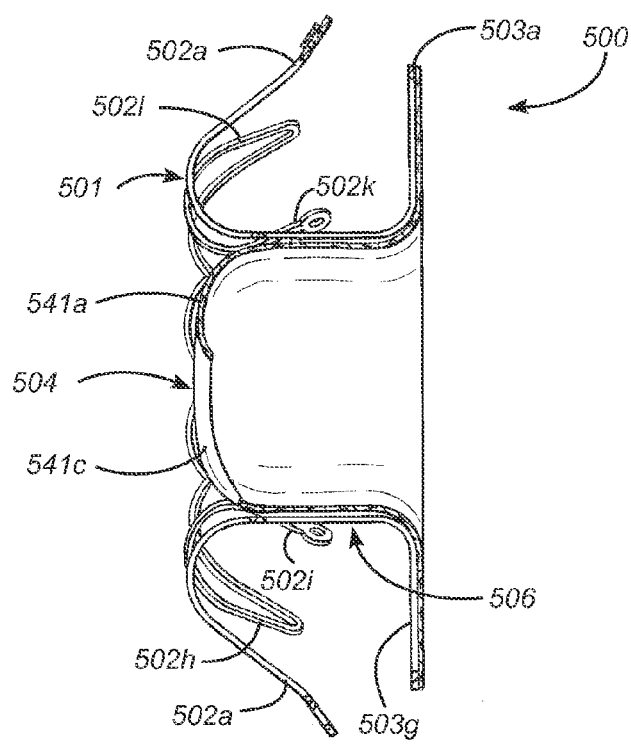
FIG. 25 is a cross-sectional side view taken along line 25-25 of FIG. 24.

Referring now to FIGS. 24 and 25 an alternate embodiment of interatrial pressure vent 500 is shown. In embodiments, flow control element 504 is comprised of leaflets 541*a-c*. Body element 501 is comprised of core segment 506 and flange segments 502*a-1* and 503*a-1* (not fully visible in FIG. 25); the number of flange segments being a multiple of the number of leaflets. This configuration improves the symmetry of strain against the flow control leaflets and also improves the uniformity of motion by the flow control element to changes in blood flow.

In embodiments the number of leaflets comprising the flow control element is three and the number of flange segments on each side of the core segment is twelve. In embodiments, the number of leaflets comprising the flow control element is three and the number of flange segments on each side of the core segment is nine. In embodiments, the number of leaflets comprising the flow control element is three and the number of flange segments on each side is six.

In embodiments, the number of leaflets comprising the flow control element is three and the number of flange segments on each side is three. In embodiments, the number of leaflets comprising the flow control element is three, the number of flange segments on one side of the core segment is twelve and the number of flange segments on the other side of the core segment is nine. In embodiments, the number of leaflets comprising the flow control element is three, the number of flange segments on one side of the core segment is twelve and the number of flange segments on the other side of the core segment is six.

In embodiments, the number of leaflets comprising the flow control element is three, the number of flange segments on one side of the core segment is twelve and the number of flange segments on the other side of the core segment is three. In embodiments, the number of leaflets comprising the flow control element is three, the number of flange segments on one side of the core segment is nine and the number of flange segments on the other side of the core segment is six. In embodiments, the number of leaflets comprising the flow control element is three, the number of flange segments on one side of the core segment is nine and the number of flange segments on the other side of the core segment is three.

In embodiments, the number of leaflets comprising the flow control element is three, the number of flange segments on one side of the core segment is six and the number of flange segments on the other side of the core segment is three. In embodiments, the number of leaflets comprising the flow control element is two and the number of flange segments on each side of the core segment is twelve. In embodiments, the number of leaflets comprising the flow control element is two and the number of flange segments on each side of the core segment is ten. In embodiments, the number of leaflets comprising the flow control element is two and the number of flange segments on each side of the core segment is eight.

In embodiments, the number of leaflets comprising the flow control element is two and the number of flange segments on each side of the core segment is six. In embodiments, the number of leaflets comprising the flow control element is two and the number of flange segments on each side of the core segment is four. In embodiments, the number of leaflets comprising the flow control element is two and the number of flange segments on each side of the core segment is two.

In embodiments, the number of leaflets comprising the flow control element is two, the number of flange segments on one side of the core segment is twelve and the number of flange segments on the other side of the core segment is ten. In embodiments, the number of leaflets comprising the flow control element is two, the number of flange segments on one side of the core segment is twelve and the number of flange segments on the other side of the core segment is eight. In embodiments, the number of leaflets comprising the flow control element is two, the number of flange segments on one side of the core segment is twelve and the number of flange segments on the other side of the core segment is six.

In embodiments, the number of leaflets comprising the flow control element is two, the number of flange segments on one side of the core segment is twelve and the number of flange segments on the other side of the core segment is four. In embodiments, the number of leaflets comprising the flow control element is two, the number of flange segments on one side of the core segment is twelve and the number of flange segments on the other side of the core segment is two. In embodiments, the number of leaflets comprising the flow control element is two, the number of flange segments on one side of the core segment is ten and the number of flange segments on the other side of the core segment is eight.

In embodiments, the number of leaflets comprising the flow control element is two, the number of flange segments on one side of the core segment is ten and the number of flange segments on the other side of the core segment is six. In embodiments, the number of leaflets comprising the flow control element is two, the number of flange segments on one side of the core segment is ten and the number of flange segments on the other side of the core segment is four. In embodiments, the number of leaflets comprising the flow control element is two, the number of flange segments on one side of the core segment is ten and the number of flange segments on the other side of the core segment is two.

In embodiments, the number of leaflets comprising the flow control element is two, the number of flange segments on one side of the core segment is ten and the number of flange segments on the other side of the core segment is two. In embodiments, the number of leaflets comprising the flow control element is two, the number of flange segments on one side of the core segment is eight and the number of flange segments on the other side of the core segment is six. In embodiments, the number of leaflets comprising the flow control element is two, the number of flange segments on one side of the core segment is eight and the number of flange segments on the other side of the core segment is four.

In embodiments, the number of leaflets comprising the flow control element is two, the number of flange segments on one side of the core segment is eight and the number of flange segments on the other side of the core segment is two. In embodiments, the number of leaflets comprising the flow control element is two, the number of flange segments on one side of the core segment is six and the number of flange segments on the other side of the core segment is four. In embodiments, the number of leaflets comprising the flow control element is two, the number of flange segments on one side of the core segment is six and the number of flange segments on the other side of the core segment is two.

In embodiments, the number of leaflets comprising the flow control element is two, the number of flange segments on one side of the core segment is four and the number of flange segments on the other side of the core segment is two.

Figure 26:
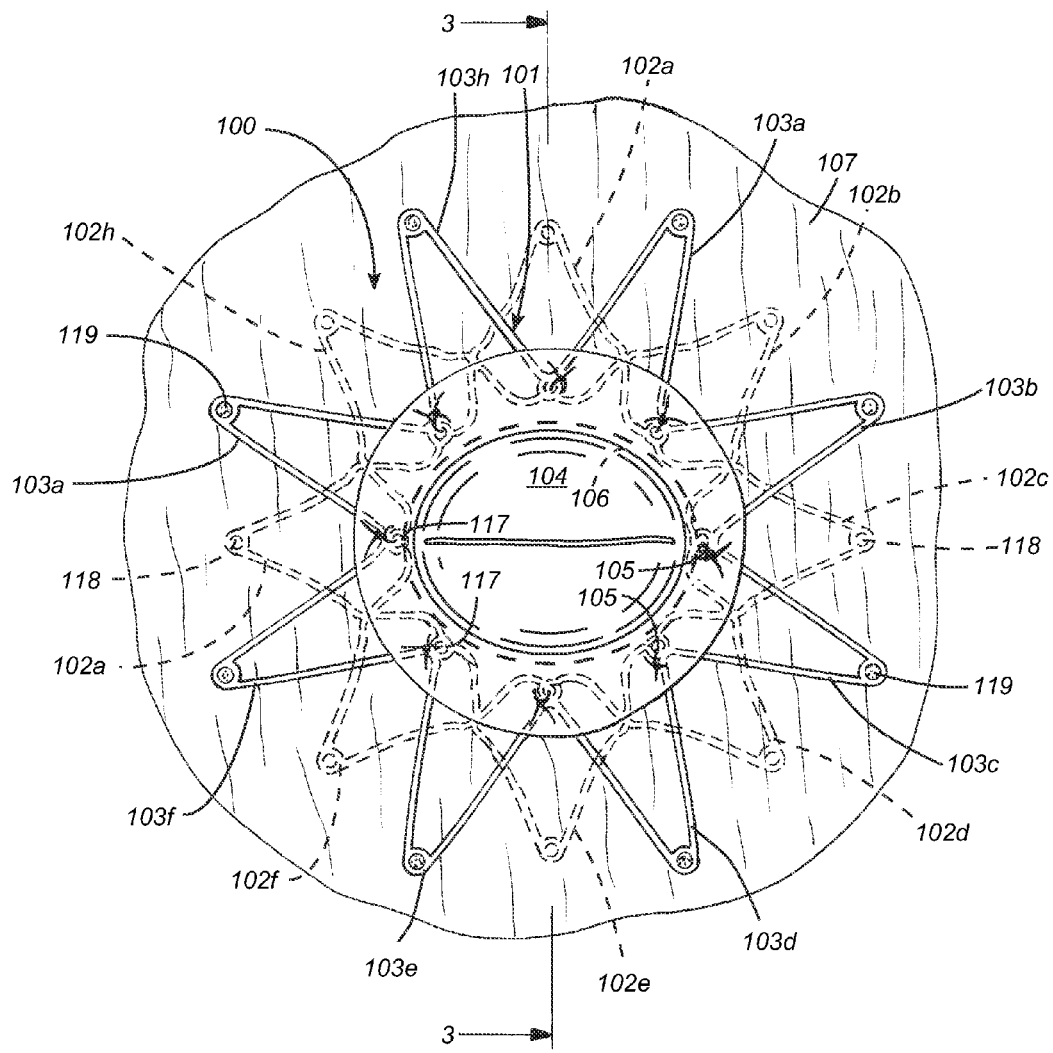
FIG. 26 shows and alternate embodiment wherein the core segment 106 is ovular rather than circular and thus the core segment is a cylindroid or elliptic cylinder rather than a simple cylinder.

FIG. 26 shows and alternate embodiment wherein the core segment 106 is ovular rather than circular and thus the core segment is a cylindroid or elliptic cylinder rather than a simple cylinder. This embodiment is more conducive to a bicuspid (or "duckbill", bivalve, or two-leaflet) configuration for the flow control element. The duckbill configuration is generally referred to as flow control element 104 in this figure. The inventors have found that the bi-valve configuration is able to open more fully when coupled with a core segment in the shape of a cylindroid.

Figure 27:
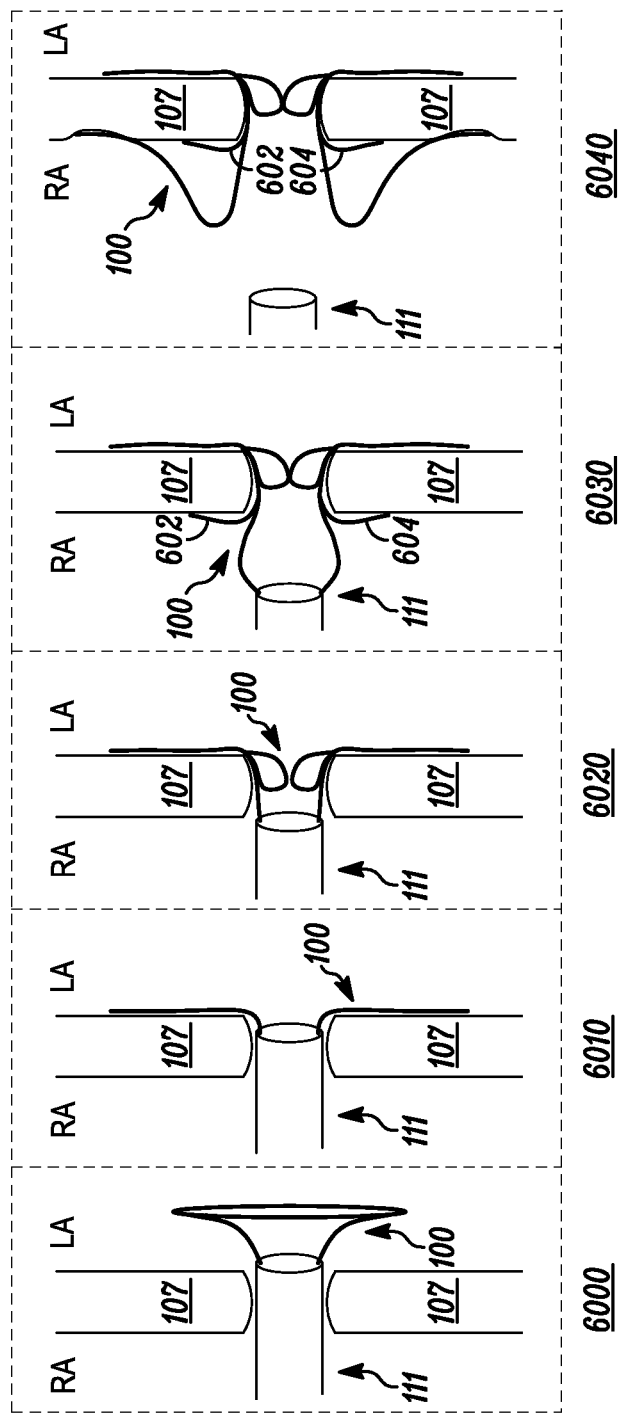
FIG. 27 is schematic depiction of another embodiment of a placement catheter system and interatrial pressure device along with the deployment process therefor.
Figure 27A:
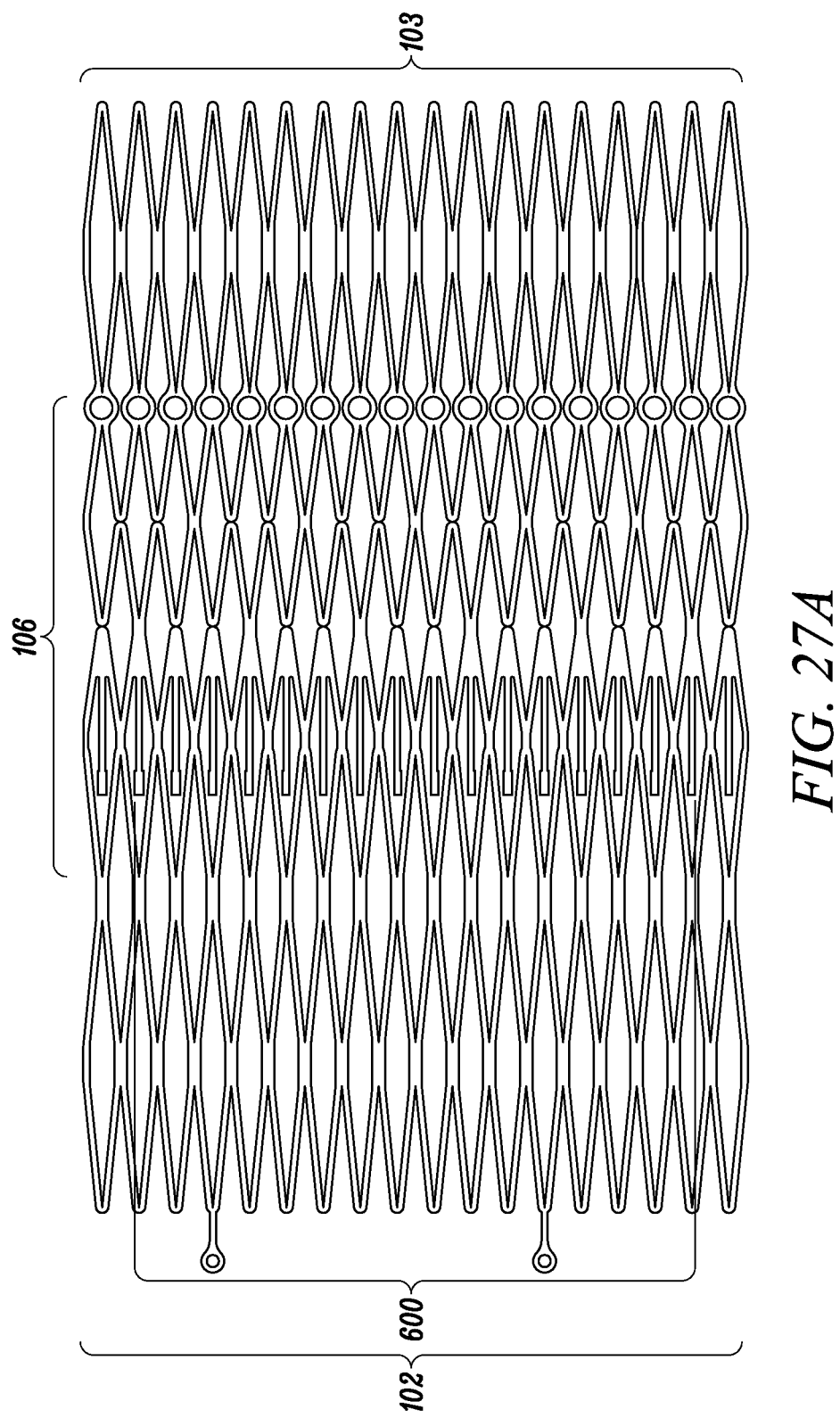
FIG. 27A is a side elevational view of the embodiment described in connection with FIG. 27 in the stowed position.

FIGS. 27 and 27A show another embodiment of an interatrial device having intermediate flange segments for a more secured fit against the septal wall. In embodiments, the intermediate flange segments are part of another a third annular flange situated on the same side of the septal wall as one of the other flanges. Reference numerals 6000 through 6040 refer to steps in the deployment of such an embodiment and will be discussed in connection with the structural features of the embodiment to illustrate this embodiment's utility and operation. The deployment process is similar to those described above, and to any commonly-known catheter based delivery process and as such the details of the process will not be discussed herein. Steps 6000 to 6020 show the deployment process steps proceeding in much the same manner as described herein. At step 6030, intermediate flange segments 602 and 604 of intermediate (or third) annular flange are deployed on the RA side. In this embodiment, intermediate flange segments 602 and 604 are shorter than the majority of the flange segments of the RA-side flange. As such, segments 602 and 604 are deployed prior to other longer segments and contact the septal wall 107 at points closer to the septal opening than the contact points of the longer segments. In this manner, the intermediate segments 602 and 604 (and the flange which they comprise) provide increased stability of the device. Any number of intermediate segments may be used although it is preferable to have at least two. As with other embodiments, the stiffness of the intermediate segments may be altered so as to differ from other flange segments of the device to avoid damage to the septal wall, i.e., lesser stiffness/greater flexibility, or to provide increased stability, i.e., greater stiffness/lesser flexibility. The choice of stiffness/flexibility variations must be balanced against the desired goals.

FIG. 27A is a side elevational view of embodiment discussed in connection with FIG. 27. In FIG. 27A the pressure venting device in its stowed configuration. Flanges 102 and 103 are shown with the flange segments that comprise them (flange segments not individually labeled). Core segment is again shown as 106. At a point between the end of the core segment 106 and proximal end of the RA side flange segment 102, the intermediate segments (collectively referred to as 600) emerge. Intermediate segments may be integral with the venting device or attached thereto in the manners described above.

Figure 28A:
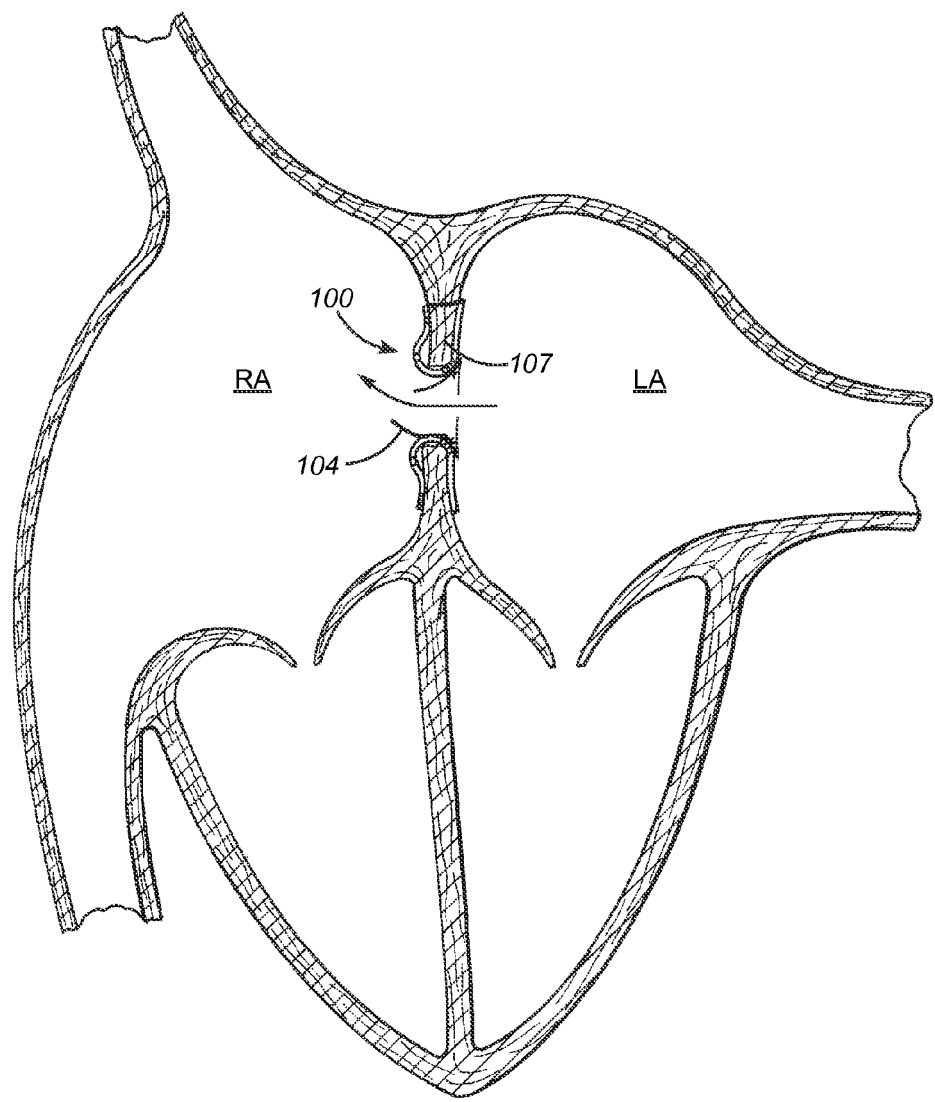
FIGS. 28A through 28C depict other embodiments of the device that direct the flow of blood in a desired direction.
Figure 28C:
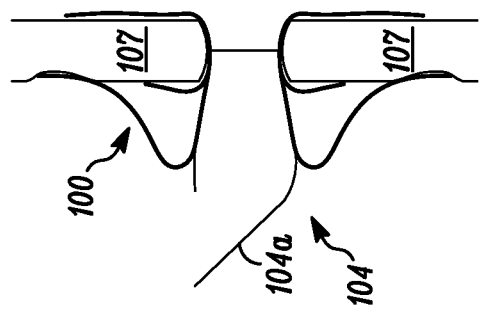
Figure 28B:
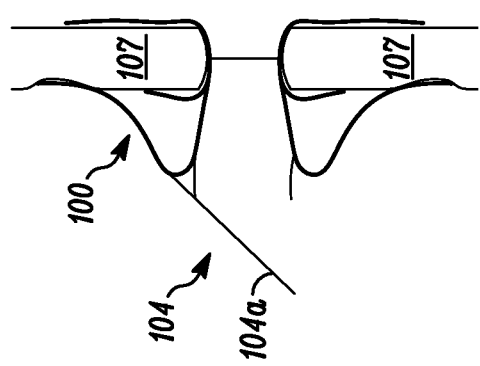

In other embodiments, the flow control element is configured to direct the blood flow in a desired direction. FIGS. 28A through 28C show such embodiments. In FIG. 28A interatrial device 100 is shown implanted in the atrial septum 107 of the heart in the same manner as shown in FIG. 1. Flow control element 104 is configured to aim the shown in this figure as in the direction toward the superior vena cava. FIGS. 28B and 28C show a more detailed view of embodiments that enable the flow to be directed in a desired direction. As shown in FIG. 28B, flow control element comprises a baffle-like flange 104a that extends at a downward angle and in the corresponding direction. In use, such embodiment directs the flow downward. FIG. 28C shows an embodiment where the flow is directed upward. The valve material (e.g. material for leaflets) of the present invention can be sized and secured to the 100 in manner to direct the flow. For example, the flow control element may contain a curved tubular member whose opening points toward the direction of flow, or the flow control element may otherwise comprise an opening directed at the area of interest. In embodiments with baffles, the stiffness of the baffle 104a may be varied, for example, made stiffer. The length of the baffle can also be varied depending on the desired flow direction. The baffle can be a separate member attached to the flow control element or it may be made of the material and/or integral with the remainder of the flow control element.

Figure 29A:
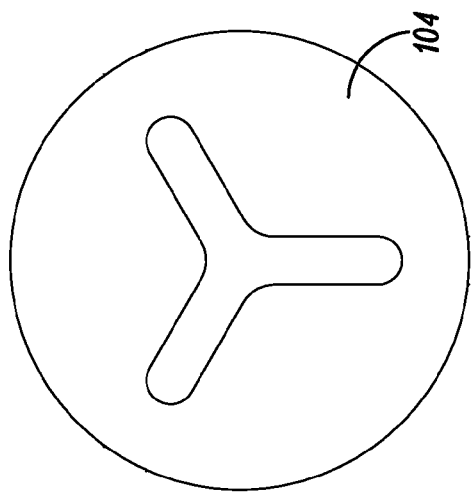
FIGS. 29A through C show exit profile shapes of the flow control element of embodiments, as viewed from the RA side.
Figure 29B:
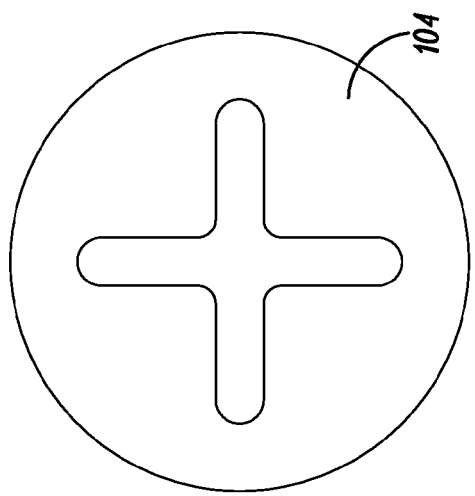
Figure 29C:
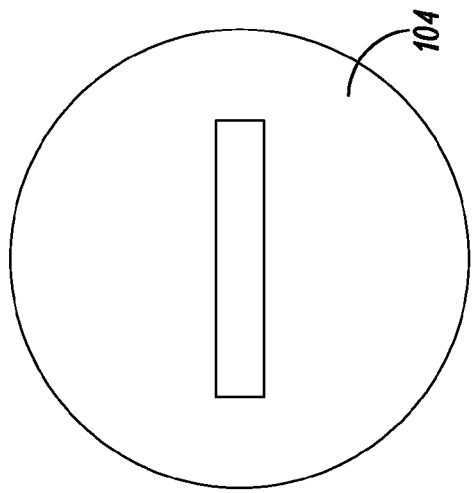

FIGS. 29A through C show exit profile shapes of the flow control element 104. In these figures, the flow control element 104 is being viewed from the RA side and thus the direction of flow is understood to coming out of the page at an angle substantially normal to the page. If the flow control element is a valve as described herein, folding and suturing patterns may be employed to achieve these exit profile shapes. In other embodiments, the end of the flow control element may be provided with a plate, or a partially frustoconical end piece, having an opening defining the two-dimensional shape shown in the Figure. The skilled artisan will appreciate that other exit profile shapes may be fashioned. The selection of an exit profile shape may provide advantages such as directing flow, preventing thrombi from moving across the septal divide, and/or reducing injury to surrounding tissue.

Figure 30:
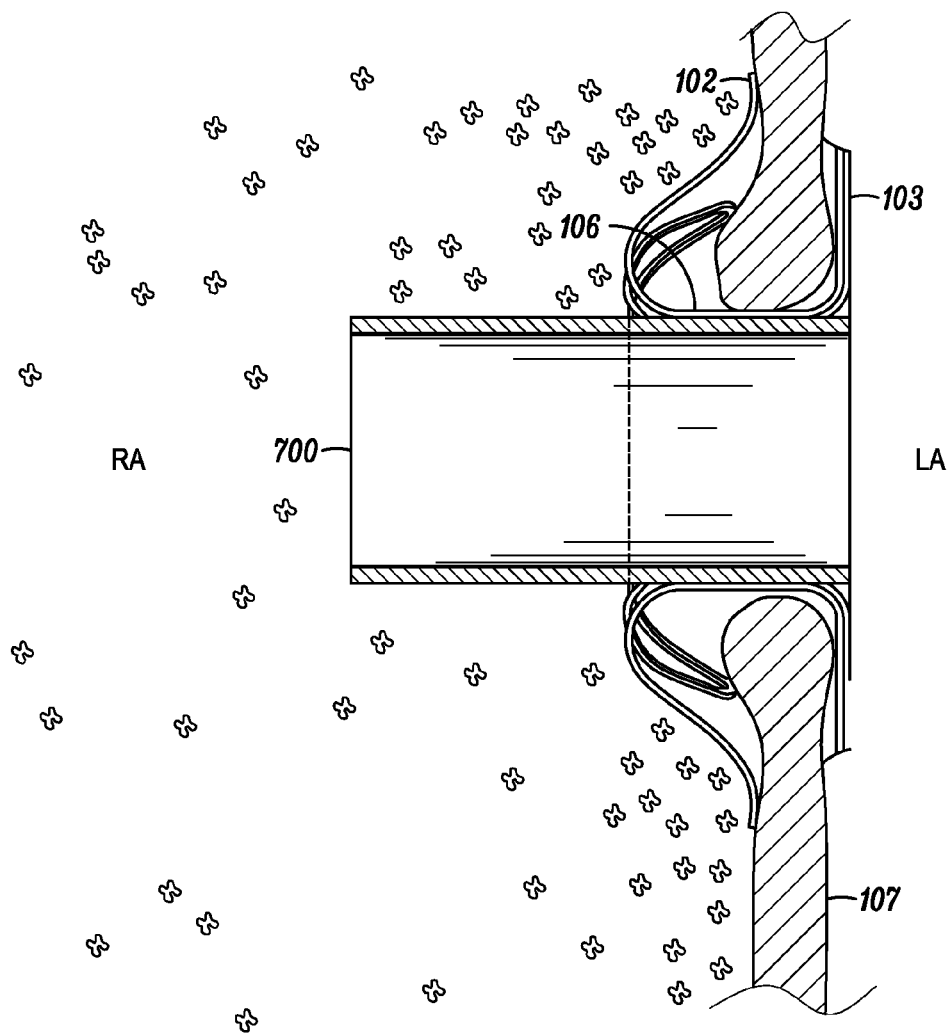
FIG. 30 is a side view of an embodiment of the device having a tube-like extension into the RA side of the heart.

Another embodiment of the invention is shown in FIG. 30. In this embodiment, the core segment 106 and flanges 102 and 103 of the device are substantially similar those described herein. Instead of the flow control elements described above (or in addition thereto) a tube-like member 700 is secured to the core segment 106. The tube member 700 is attached to the core segment 700 in a manner to allow the RA end of tube to extend into the RA in an axial direction, thus the tube's length must be sufficient to extend a distance into the RA. It has been found that the tube 700 configured in this manner prevents embolic particles from entering the tube and crossing over the septal divide into the LA. The distance that the tube 700 extends into the RA and beyond the plane of the RA-side flange opening (indicated by dotted line) should be at least a 1 mm but may be up to 2 cm in preferable embodiments. Even at relatively short lengths (such as where the tube extends only a few millimeters into the RA), the inventors have noted the surprisingly unexpected result of a reduction of embolic particles passing through. This is due to, in part, the tendency of embolic particles to collect along the surface of the septal wall and move toward the septal opening (or opening of an implanted device) with each cycle of the heart. By extending away from the septal wall 107, the tube provides an effective barrier to the embolic particles that would otherwise travel toward and possibly through the septal opening.

Although the present invention has been described and illustrated in the foregoing exemplary embodiments, it is understood that the present disclosure has been made only by way of example, and that numerous changes in the details of implementation of the invention may be made without departing from the spirit and scope of the invention, which is limited only by the claims which follow.

What is claimed is:

1. A device for implanting in an opening in a septal wall in a heart of a patient, comprising:
   i. a first annular flange comprising a plurality of flange segments, each of said flange segments of the first annular flange having a first end and a second end;
   ii. a second annular flange comprising a plurality of flange segments, each of said flange segments of the second annular flange having a first and a second end, at least one of said flange segments of said second annular flange comprising a end adapted to be substantially parallel with and contact the septal wall when deployed; and
   iii. a core segment having a first diameter when deployed, said core segment defining a passage adapted to permit fluid to flow therethrough from one side of said septal wall to another side of said septal wall,
      wherein the first ends of the first annular flange and the first ends of the second annular flange are contiguous with and define the core segment,
      wherein at least one of the flange segments of the second annular flange includes a first section that extends into the atrium and a second section that extends from the first section toward the septal wall,
      wherein the second end of the at least one of the flange segments of the second annular flange is adapted to be in contact with the septal wall,
      wherein at least a portion of at least one of said flange segments is more flexible than a portion of said core segment, and
      wherein the core segment is collapsible, enabling the core segment to have a second diameter less than the first diameter thereby enabling percutaneous delivery.

2. The device of claim 1 further comprising a flow control element having two sides and attached to said core segment.

3. The device of claim 2, wherein said flow control element opens upon an occurrence of a pressure differential between said two sides of said flow control element.

4. The device of claim 3, wherein said flow control element allows fluid to flow through said passage from an area of higher pressure to an area of lower pressure.

5. The device of claim 4, wherein said pressure differential is at least 2 mm Hg.

6. The device of claim 1, wherein each of said plurality of flange segments comprises a radiopaque marker.

7. The device of claim 2, wherein said core segment comprises a plurality of suture holes and wherein said flow control element is sutured to a selected number of said suture holes.

8. The device of claim 7, wherein said selected number of suture holes defines at least one of an entry and exit profile of the flow control element.

9. The device of claim 2, wherein said flow control element is a valve.

10. The device of claim 9, wherein said valve comprises at least two leaflets.

11. The device of claim 10, wherein at least one of the leaflets is more flexible than another of said at least two leaflets.

12. The device of claim 1, wherein said septal wall is the atrial septum of said patient's heart.

* * * * *